US008514398B2

(12) United States Patent
Pang et al.

(10) Patent No.: US 8,514,398 B2
(45) Date of Patent: Aug. 20, 2013

(54) SENSING DEVICES AND TECHNIQUES USING 3-D ARRAYS BASED ON SURFACE PLASMON EXCITATIONS

(75) Inventors: Lin Pang, San Diego, CA (US); Haiping Matthew Chen, La Jolla, CA (US); Yeshaiahu Fainman, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 365 days.

(21) Appl. No.: 12/943,916

(22) Filed: Nov. 10, 2010

(65) Prior Publication Data

US 2012/0105853 A1 May 3, 2012

Related U.S. Application Data

(60) Provisional application No. 61/259,972, filed on Nov. 10, 2009.

(51) Int. Cl.
*G01N 21/55* (2006.01)
*G01N 21/00* (2006.01)
*H01J 49/00* (2006.01)

(52) U.S. Cl.
USPC ........ 356/445; 356/244; 356/301; 422/82.05; 422/82.11; 250/286; 250/297

(58) Field of Classification Search
None
See application file for complete search history.

(56) References Cited

U.S. PATENT DOCUMENTS

2006/0034729 A1* 2/2006 Poponin ..................... 422/82.05
2008/0278728 A1* 11/2008 Tetz et al. .................... 356/445

OTHER PUBLICATIONS

Chen, H.M., et al., "Three-dimensional composite metallodielectric nanostructure for enhanced surface plasmon resonance sensing," Applied Physics Letters, 94(7):073117(1-3), Feb. 2009.
Eftekhari, F., et al., "Nanoholes as Nanochannels: Flow-through Plasmonic Sensing," Analytical Chemistry, 81 (11):4308-4311, Jun. 2009.
Im, H., et al., Vertically Oriented Sub-10-nm Plasmonic Nanogap Arrays, Nano Letters, 10(6):2231-2236, May 2010.
Pang, L., et al., "Controlled detection in composite nanoresonant array for surface plasmon resonance sensing," Optics Express, 17(17):14700-14709, Aug. 2009.
Pang, L., et al., "Spectral sensitivity of two-dimensional nanohole array surface plasmon polariton resonance sensor," Applied Physics Letters, 91(12):123112(1-3), Sep. 2007.
Yanik, A.A., et al., "Integrated nanoplasmonic-nanofluidic biosensors with targeted delivery of analytes," Applied Physics Letters, 96(2):021101(1-3), Jan. 2010.

* cited by examiner

*Primary Examiner* — Neil N Turk
(74) *Attorney, Agent, or Firm* — Perkins Coie LLP

(57) ABSTRACT

Techniques, apparatus, material and systems are described for implementing a three-dimensional composite mushroom-like metallodielectric nanostructure. In one aspect, a surface plasmon based sensing device includes a substrate and a layer of an anti-reflective coating over the substrate. The surface Plasmon based sensing device includes a dielectric material on the anti-reflective coating shaped to form a 2-dimensional array of nanoholes spaced from one another. Also, the surface Plasmon based sensing device includes a layer of a metallic film formed on the 2-dimensional array of nanoholes to include openings over the nanoholes, respectively, wherein the sensing device is structured to support both propagating surface plasmon polariton (SPP) waves and localized surface plasmon resonant (LSPR) modes.

11 Claims, 22 Drawing Sheets

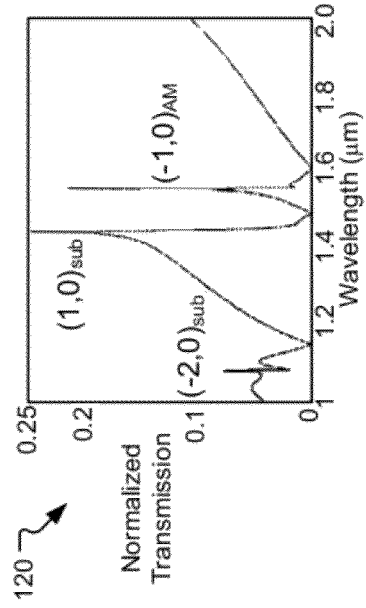
Figure 1b
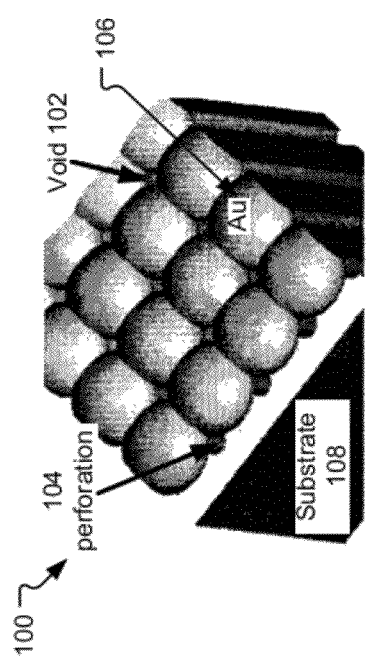
Figure 1a
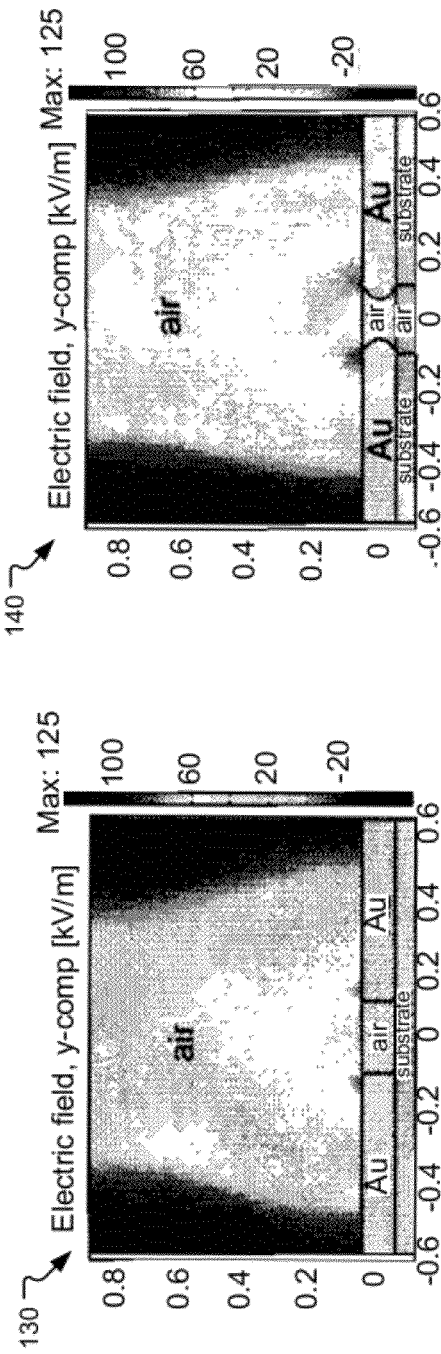
Figure 1d
Figure 1c

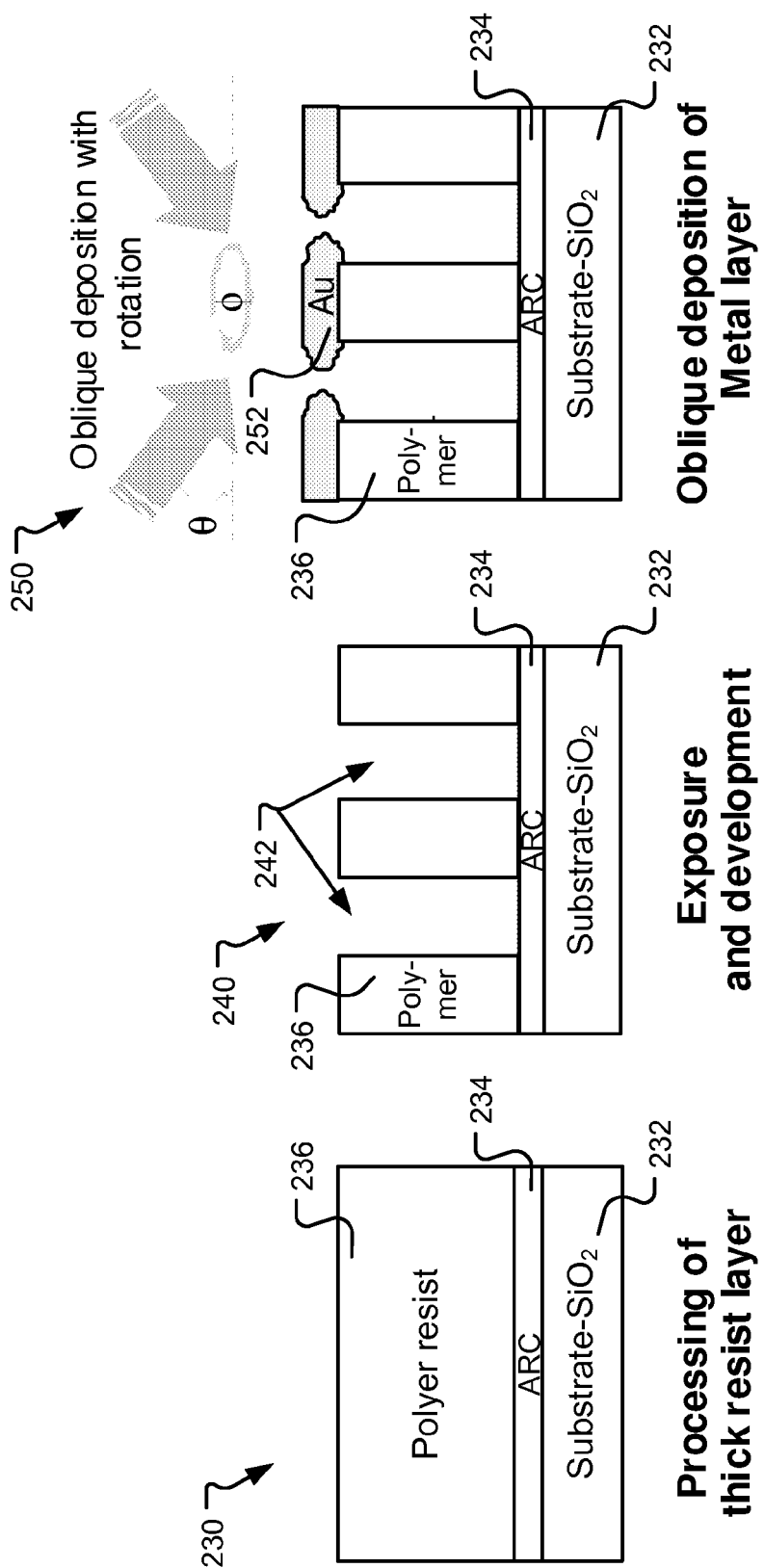

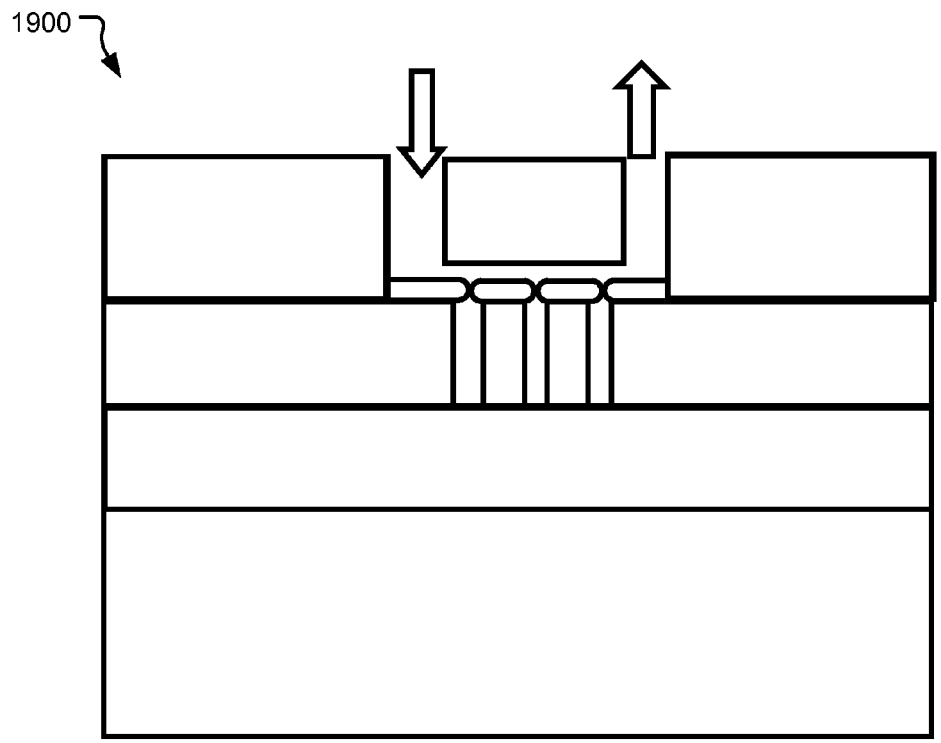
Figure 19a
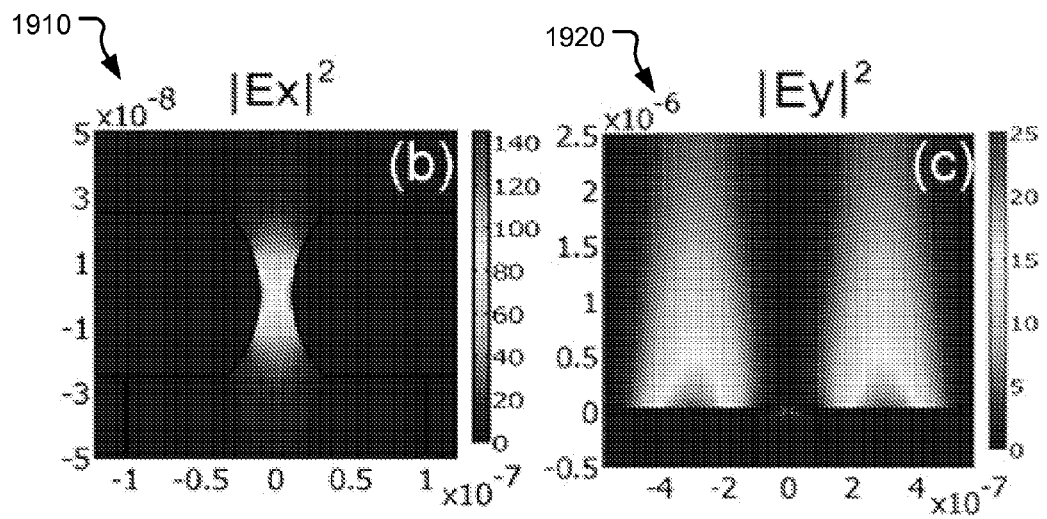
Figure 19b
Figure 19c

SENSING DEVICES AND TECHNIQUES USING 3-D ARRAYS BASED ON SURFACE PLASMON EXCITATIONS

CROSS-REFERENCE TO RELATED APPLICATIONS

This application claims benefit of U.S. Provisional Patent Application No. 61/259,972, filed Nov. 10, 2009, the entire content of which is incorporated by reference.

FEDERALLY SPONSORED RESEARCH OR DEVELOPMENT

This invention was made with government support under Grant No. ECS0608863 awarded by the National Science Foundation and Grant Nos. 67L-1083656 and HR0011-04-1-0032 awarded by the Defense Advanced Research Projects Agency. The government has certain rights in the invention.

BACKGROUND

This document relates to sensing devices and sensing techniques and their applications in sensing and detecting various materials, including chemical and biological substances.

Plasmons are eigenmodes of collective density oscillations of quasi-free electrons or an electronic gas in metals and other materials under optical excitation. Surface plasmons can be generated by coupling photons and electrons at or near a surface of an electrically conductive material as surface plasmon polaritons (SPPs). In addition, surface plasmons can be excited or generated as localized surface plasmon resonance (LSPR) for nanometer-sized metallic structures.

Some surface plasmon resonant (SPR) sensors use propagating SPP in sensing the refractive index change surrounding the metallic surface or nanostructure. One such sensor is the SPP sensor in the Kretschmann configuration which uses a high refractive index prism for evanescent coupling under a large incident angle to excite the liquid-metallic SPP wave on the liquid metal interface, and grating configuration, both reflection and transmission, which uses grating wavevector matching condition to excite propagating SPPs on the interface of liquid and metallic grating. In such SPP sensing devices, the excited electric field is distributed on an extended surface area, so no 'hot spot' or concentrated electric field exists.

Other surface plasmon resonant (SPR) sensors use LSPP in sensing the refractive index change surrounding the metallic surface or nanostructure. For example, one such LSPP sensor includes nanoparticle scattering and random nanohole transmission configurations, which utilize the nanoresonant excitations induced by the particle's size and shape to sense the refractive index change around the nanostructures. In many implementations of such LSPP sensors, only "hot spot" exists as nanoresonance itself; however, there is little electric field on areas where nanostructures are absent. In addition, the excitation efficiency of LSPP is low due to the nanostructure's size and small portion of phase matching condition.

SUMMARY

Techniques, apparatus and systems are described for implementing a 3-dimensional composite metallodielectric nanoresonant array of nanoholes.

In one aspect, a surface plasmon based sensing device includes a substrate and a layer of an anti-reflective coating over the substrate. The surface plasmon based sensing device includes a dielectric material on the anti-reflective coating shaped to form a 2-dimensional array of nanoholes spaced from one another. Also, the surface plasmon based sensing device includes a layer of a metallic film formed on the 2-dimensional array of nanoholes to include openings over the nanoholes, respectively. The sensing device is structured to support both propagating surface plasmon polariton (SPP) waves and localized surface plasmon resonant (LSPR) modes.

Implementations can optionally include one or more of the following features. The metal layer can include a layer of gold formed to control a size of the openings.

In another aspect, a surface plasmon based sensing device can include a substrate and a layer of an anti-reflective coating over the substrate. The surface Plasmon based sensing device can include a dielectric material formed on the anti-reflective coating shaped to form a 3-dimensional composite metallodielectric nanoresonant array of nanoholes spaced from one another. Also, the surface plasmon based sensing device includes a layer of a metallic film formed on the 3-dimensional composite metallodielectric nanoresonant array of nanoholes to include openings over the nanoholes respectively. The 3-D composite metallodielectric nanoresonant array is structured to support both propagating surface plasmon polariton (SPP) waves and localized surface plasmon resonant (LSPR) modes.

Implementations can optionally include one or more of the following features. The metal layer can include a layer of gold formed to control a size of the openings.

The described devices can be fabricated using a fabrication method in another aspect. The fabrication method includes applying a polymer resist over a substrate. The method also includes forming an array of nanoholes in the polymer resist. A metal layer is formed over the formed array of nanoholes using an oblique metal deposition process to include openings over the nanoholes. The oblique metal deposition process includes depositing the metal layer from an oblique angle while rotating the substrate.

Implementations can optionally include one or more of the following features. Applying the polymer resist can include spin-coating a layer of the polymer resist material on the substrate. Forming the array of nanoholes can include forming the nanohole array in the polymer resist material using holographic lithography. The fabrication method can include applying an anti-reflective coating between the substrate and the polymer resist material. Also, the metal layer can be removed and another metal layer can be applied to change a size of the openings over the nanoholes. The metal layer can include gold.

In another aspect, a method of fabricating a nanostructure device can include depositing a dielectric layer over a substrate. The method can include depositing a silicon membrane layer over the dielectric layer, and depositing a photoresist layer over the membrane layer. Also, the photoresist layer is patterned to generate a nanohole structure that includes multiple nanoholes. Dry etching is used to pattern the silicon membrane layer below the patterned photoresist layer. Wet etching is used to remove portions of the dielectric layer to create a channel. Using oblique deposition, a metal layer is formed on top of the nanohole structure of the photoresist layer to include openings over the nanoholes. Also, a fluidic channel is integrated over the nanostructure.

Implementations can optionally include one or more of the following features. A size of the openings over the nanoholes can be controlled.

In another aspect, a surface plasmon based sensing device includes a substrate and a dielectric layer deposited over the substrate. A silicon membrane layer is deposited over the dielectric layer. A photoresist layer is deposited over the membrane layer and patterned to form a 3-dimensional composite metallodielectric nanoresonant array of nanoholes spaced from one another. A layer of a metallic film is formed on the 3-dimensional composite metallodielectric nanoresonant array of nanoholes to include openings over the nanoholes respectively. The metal film is deposited using oblique deposition, and a fluidic channel is integrated over the nanostructure.

Implementations can optionally include one or more of the following features. The 3-D composite metallodielectric nanoresonant array can be structured to couple propagating surface plasmon polariton (SPP) waves and localized surface plasmon resonant (LSPR) modes. Coupling SPP and LSPR can include configuring the 3-D composite metallodielectric nanoresonant array to use an enhanced surface electric field and micro-channel configuration to sense a molecule of interest. Coupling SPP and LSPR can include configuring the 3-D composite metallodielectric nanoresonant array to monitor at least one location of the nanoholes to detect molecules near the nanoholes. Coupling SPP and LSPR can include configuring the 3-D composite metallodielectric nanoresonant array in a through-hole fluidic configuration to detect small molecules. The 3-D composite metallodielectric nanoresonant array can be configured in a pass-through configuration to allow molecules to pass through the nanoholes so as to allow the molecules to sense a maximal local electric field and yield maximal enhancement Raman detection. The 3-D composite metallodielectric nanoresonant array can be configured in a pass-over configuration that includes a microfluidic channel over the 3-D composite metallodielectric nanoresonant array to allow molecules to pass over the nanoholes. The 3-D composite metallodielectric nanoresonant array can be configured to monitor SPP resonant shift over an area on the 3-D composite metallodielectric nanoresonant array surface to obtain quantity information of molecules on the surface; and monitor Raman scattering from the nanoholes of the 3D metallodielectric nanoresonant array to identify the molecules. The 3-D composite metallodielectric nanoresonant array can be configured to monitor LSPR resonant shift over a single or multiple nanoholes to obtain quantity information of molecules near the nanoholes; and monitor Raman scattering from the nanoholes of the 3D metallodielectric nanoresonant array to fast identify the molecules.

Implementations of the described techniques, apparatus and systems can potentially provide one or more of the following advantages. The fabricated mushroomlike composite metallodielectric nanostructure can show improved characteristics for surface Plasmon resonance sensing applications with an enhancement in the normal electric field. A sensor build into the composite nanostructure can be used to determine the hydrophilicity of its surface by monitoring the resonant wavelength shift and computing the corresponding adsorption thickness.

BRIEF DESCRIPTION OF DRAWINGS

FIG. 1(a) shows a schematic of the 3-D composite mushroom-like metallodielectric nanostructure.

FIG. 1(b) shows far-field RCWA simulation of nanohole array excited at 17.3 degree with periodicity of 1.20 µm and a gap size of 200 nm using a gold thickness of 100 nm.

FIG. 1(c) shows the near-field distribution for a hole array structure in a gold film with a maximum value of 87 V/m.

FIG. 1(d) shows an enhanced field distribution for the composite mushroom-like, metallodielectric nanostructure with a maximum value of 125 V/m.

FIG. 2(c) is a diagram showing an application of a photoresist layer over a substrate.

FIG. 2(d) is a diagram shown the process of exposing the resist film with holographic lithography and developing to achieve a thick perforated structure.

FIG. 2(e) shows depositing a metallic layer (e.g., gold) at an oblique angle while rotating the substrate or the sputtering source to accomplish nanoresonant structures on the perforated array structure.

FIG. 19a shows an example of the Pass Over Configuration used for large (micron) particle detection.

FIGS. 19b and 19c show LSPR and enhanced SPP.

Similar reference numbers represent similar components throughout the figures.

DETAILED DESCRIPTION

Figure 2A:
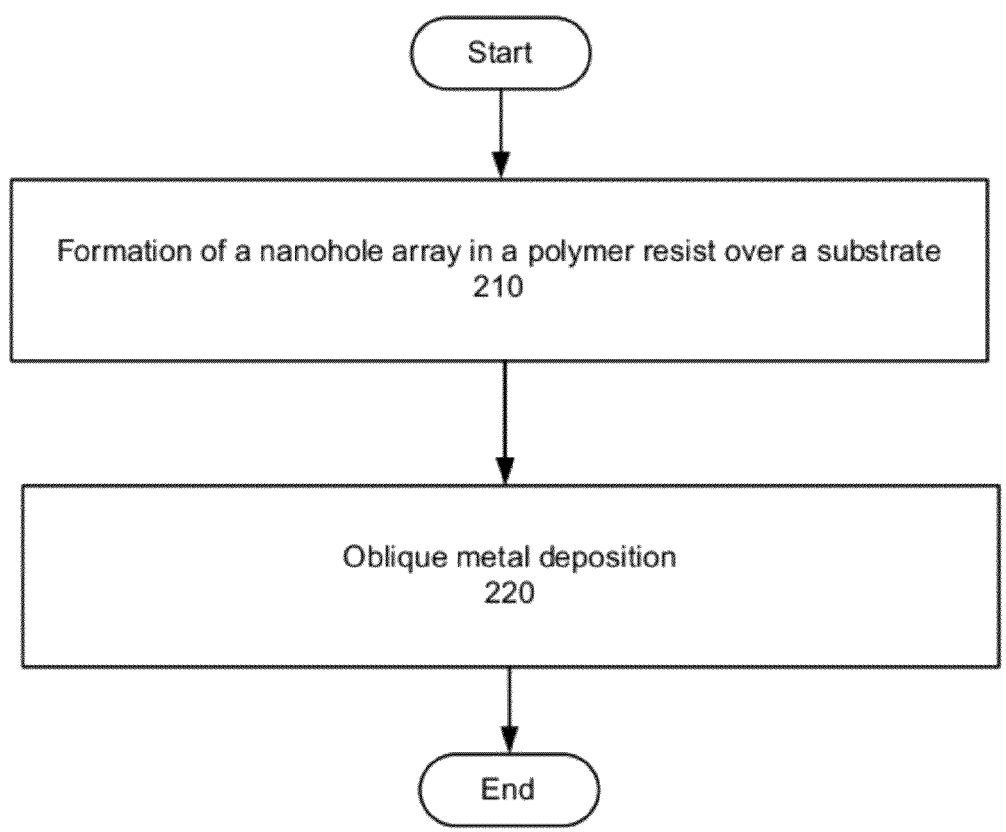
FIGS. 2(a) and 2(b) show process flow diagrams of a process for fabricating a 3-D composite mushroom-like metallodielectric nanostructure.

Sensing devices and techniques based on surface plasmons in this document are based on simultaneous excitation of both SPPs and LSPRs. The combination of both SPPs and LSPRs in the described sensing devices can be implemented to achieve one or more advantages, including but not limited to synergetic combination of two surface plasmonic resonances, propagating SPP waves and LSPR modes, effective excitations and couplings of SPPs and LSPRs achieved by exciting SPPs, which propagates along the metallic surface, and couplings to LSPRs supported by nanoresonant structures, construction of nanoresonant structures over hole array structures by depositing a controlled layer of metal at an oblique angle onto deeply perforated polymer film to realize controlled void diameter for excitation of LSPRs, while exciting and generating SPPs by the periodic structure via the wavevector matching condition; and achieving enhanced sensing applications in physical parameter and bio-recognition reactions.

A nanoresonant structure can be formed by integrating nanoparticles into a hole array structure. The periodically perforated hole array structure can be utilized to effectively excite propagating SPP wave along the metallic surface via the phase matching condition (i.e., momentum conservation). The SPP wave couples into the nanoparticles to excite LSPR around the nanoparticles to enhance the defined electric field on the metallic medium interface to increase the sensitivity of the sensing configuration. For a large area implementation, the complementary of the finely arranged nanoparticles, such as nanovoids can be used to replace the nanoparticles for excitation of LSPR for electric field enhancement.

For example, a three-dimensional composite mushroom-like metallodielectric nanostructure can be formed by a layer of structured metal (e.g., gold) film on top of a periodic perforated substrate to achieve desired coupling between propagating surface plasmon polariton wave and localized surface plasmon resonance. This 3D structure can be used for enhanced sensing applications, including surface physical property detection and bio-recognition reaction monitoring.

In operation of the present 3D structure, two SPP resonances, propagating SPP wave and localized SPP resonance, are excited simultaneously, to enhance the defined electric field on the metallic medium interface to enhance the sensitivity of the sensor. The configuration is a three-dimensional composite mushroom-like metallodielectric nanostructure, which comprises of perforated hole array and nanoresonant on the array.

The propagating SPP wave is excited by the periodically perforated hole array via the phase matching condition (i.e., momentum conservation). For the square hole array with period d in both orthogonal directions in the Cartesian coordinate system, the wave vector of the excited SPP field can be written as:

$$\vec{K}_{SP} = \frac{2\pi}{\lambda}\sin\theta(\cos\phi\vec{u}_x + \sin\phi\vec{u}_y) + p\frac{2\pi}{d}\vec{u}_x + q\frac{2\pi}{d}\vec{u}_y,$$

where $\lambda$ is wavelength in vacuum, $\theta$ is the polar angle of incident light, $\phi$ is the azimuthal angle, p and q are integers corresponding to the SPP Bloch modes, $\vec{u}_x$ and $\vec{u}_y$ are unit vectors along the x- and y-axis in the 2-D square nanohole array lattice. The excited SPP wave propagates along the metallic medium interface, hits the nanoresonances, and effectively excites the LSPRs, whose strong electric field is contained near the nanoresonances.

The three-dimensional composite mushroom-like metallodielectric nanostructure is realized by first making a periodic hole array in a thick polymer layer by using holographic lithography, then depositing a controlled metallic layer at an oblique angle on deeply perforated polymer film to realize controlled void nanostructure with controlled size. Linewidth can be controlled by varying the void size. Also, the nanostructure array can be reconfigured by stripping away the gold layer and sputtering another film with a different thickness.

FIG. 1(a) shows a schematic of the 3-D composite mushroom-like metallodielectric nanostructure 100. The nanoresonant structure can include a layer of structured gold film 106 on top of a perforated substrate 108. The gold film 106 protrudes out over the perforated substrate 108, forming nanovoids. The size of the nanovoids between the gold can be controlled independently of the underlying cylindrical perforations 104. When SPPs reflect between gold barriers, they interfere with each other and form localized standing wavers. Field localization also occurs near sharp apexes and the coupling between these two mechanisms is used to enhance the normal electric field. The LSPRs exist in the voids 102, while the SPPs exist on the gold surface. Simulation of excitation of propagating SPP waves and couplings to LSPR resonances are given in FIGS. 1(b), (c) and (d) with an example of an array with periodicity of 1.20 µm, a nanoresonant gap size of 200 nm, and gold film thickness of 100 nm with refractive index of air being 1.0 at the input and 1.5 for the glass substrate.

FIG. 1(b) shows far-field RCWA simulation of nanohole array excited at 17.3 degree with periodicity of 1.20 µm and a gap size of 200 nm using a gold thickness of 100 nm. From the SPP dispersion relation for a 2D nanohole structure with a periodicity of 1.2 µm and a laser center wavelength of 1.55 µm, the plane-wave incidence angle to excite the (−1, 0) air-metal (AM) mode occurs at 17.3°. Considering an incident beam illuminating the array from air at an angle of 17.3°, rigorous coupled wave analysis (RCWA) was used to simulate the transmission in FIG. 1(b) for a 2D nanohole array with a periodicity of 1.2 µm, a gap size of 200 nm, and a gold film thickness of 100 nm. The (−1, 0) AM mode can be excited around 1.55 µm, matching the calculation from the dispersion relation. FIG. 1(b) also shows the excitation of substrate-metal modes with a substrate index of 1.5.

The near-field distribution of the electric fields at the SPP resonance can be then simulated using the finite element method (FEM). FIG. 1(c) shows the near-field distribution for a hole array structure in a gold film with a maximum value of 87 V/m, while FIG. 1(d) shows an enhanced field distribution for the composite mushroom-like, metallodielectric nanostructure with a maximum value of 125 V/m. This enhancement is not due to the narrower opening but rather due to the couplings between the edges of the mushroom-like shape as well as localized and propagating plasmons. Furthermore, a 25-nm-thick subdomain integration of the normal electric field immediately above the gold material shows an enhancement of 1.4 times for the mushroom composite nanostructure over the hole-only array structure.

Figure 2B:
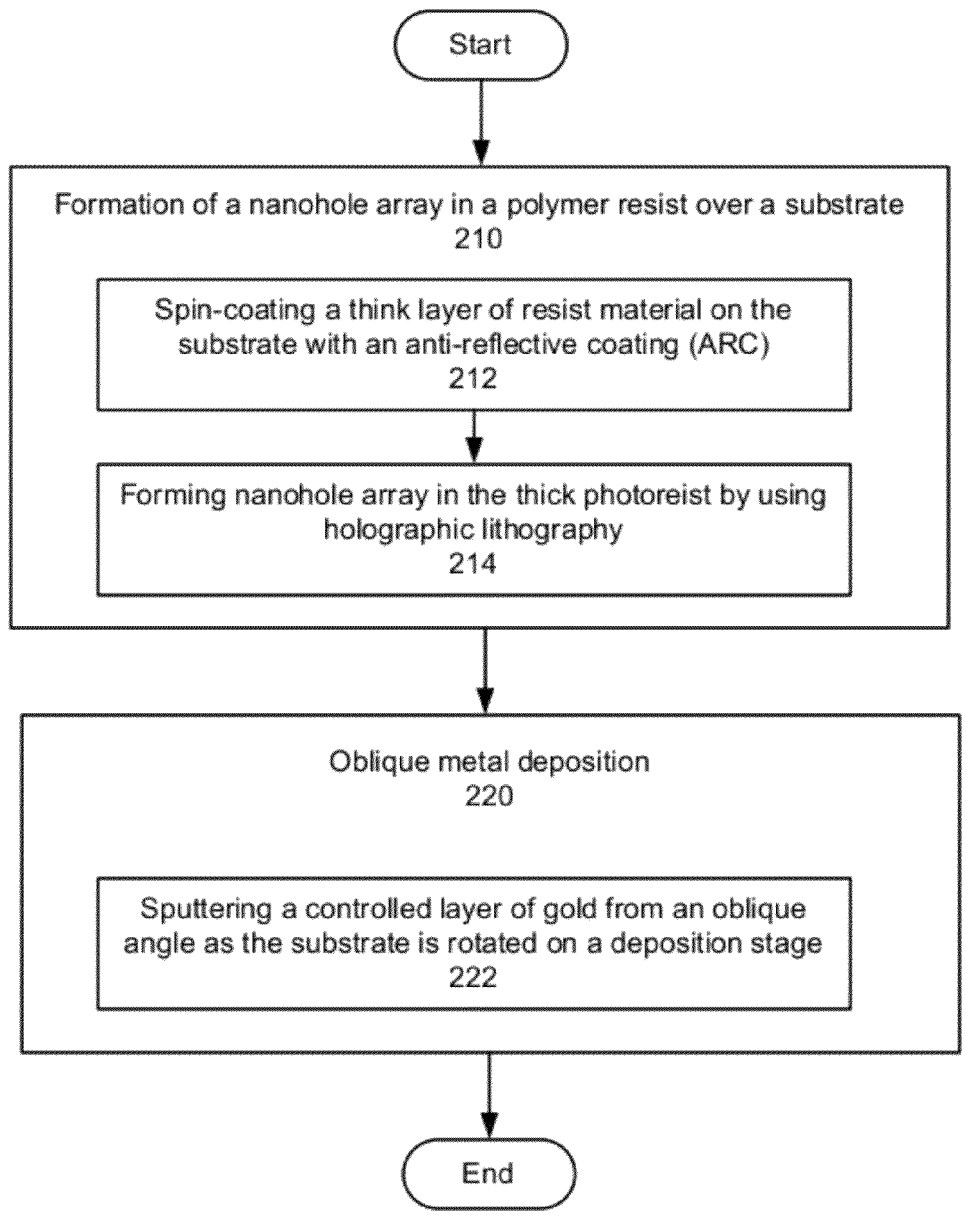

FIGS. 2(a) and 2(b) show process flow diagrams of a process for fabricating a 3-D composite mushroom-like metallodielectric nanostructure (200). Fabrication processing of 3-D composite metallodielectric nanoresonant array in this example includes formation of a nanohole array in a polymer resist applied over a substrate (210) and an oblique metal deposition step (220). In forming the nanohole array, a thick (e.g., 1-μm) layer of resist material is spin-coated on the substrate with an anti-reflective coating (ARC) for elimination of multiple reflections from the substrate (212). The nanohole array is formed in the thick photoresist by using holographic lithography (214). For example, the resist film can be exposed with holographic lithography and developed to achieve the thick perforated structure. The oblique metal deposition process is achieved by sputtering a controlled layer of gold from an oblique angle as the substrate is rotated on the deposition stage (222). The thickness of the gold layer is given by:

$$t = RT \sin \theta,$$

where R, T and θ represent the deposition rate, time, and the incidence angle of ion beam respectively. The void size can be determined by:

$$g = d - 2RT \cos t(\theta) f$$

wherein d is the periodicity in the resist and f is a filling factor, empirically calculated to be between 1.1 and 1.3. As the thickness increases, the void size decreases. Thus, the size of the void can be precisely controlled by adjusting the sputtering time. Since the void size determines the scattering rate and thus the lifetime of the SPP mode, decreasing the size gives a narrower transmission linewidth. The full width at half maximum (FWHM) of the resonant linewidth Γ directly dictates the SPR sensor's minimum resolution and resolving power with a figure of merit defined by $\chi = S/\Gamma$, where S is the sensitivity defined as the derivative of the monitored resonant parameter with respect to the refractive index unit. Thus, a narrow linewidth yields a higher figure of merit.

FIGS. 2(c), 2(d) and 2(e) are diagrams that illustrate the fabrication process 200 in realizing the 3-D composite mushroom-like metallodielectric nanostructure. FIG. 2(c) is a diagram showing an application of a photoresist layer 236 over a substrate 232. An anti-reflective coating (ARC) for elimination of multiple reflections from the substrate is applied over the substrate 232. Additionally, a thick layer of resist material 236 is applied over the ARC by spin-coating along with the ARC.

FIG. 2(d) is a diagram shown the process of exposing the resist film 236 with holographic lithography and developing to achieve a thick perforated structure. The polymer resist layer 236 shows perforations 242 as a result of the exposing and developing.

FIG. 2(e) shows depositing a metallic layer (e.g., gold) 252 at an oblique angle while rotating the substrate or the sputtering source to accomplish nanoresonant structures on the perforated array structure. The gold layer 252 is deposited over the perforated polymer resist layer and does not cover the perforations.

Figure 2F:
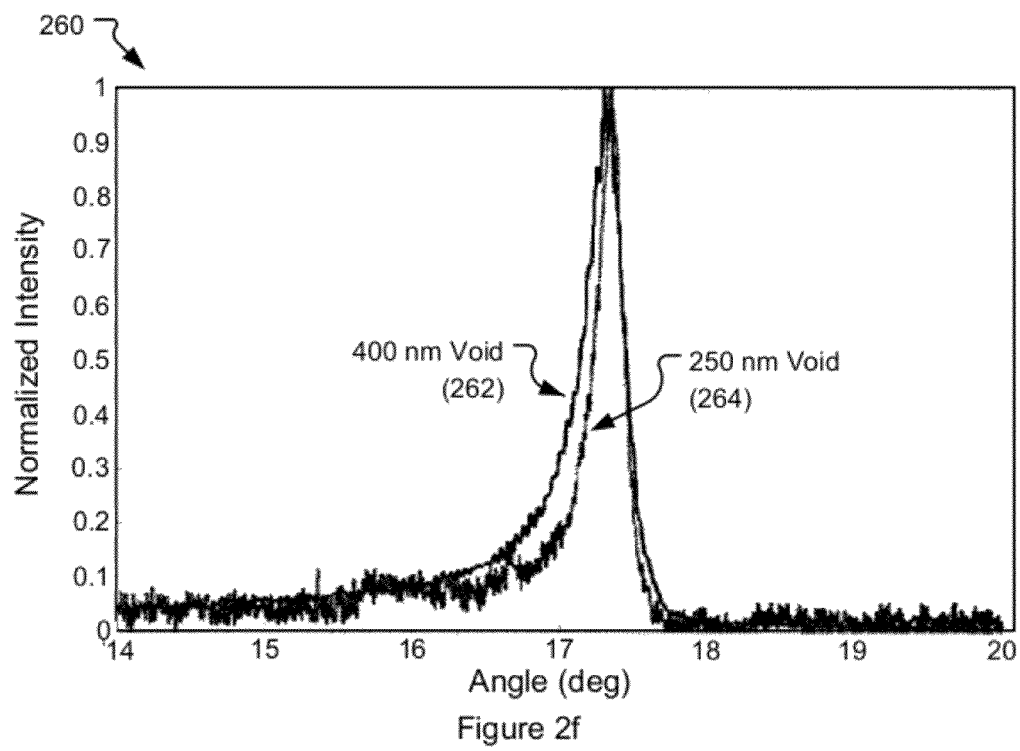
FIG. 2(f) shows transmission spectra at a wavelength of 1550 nm with void diameters of 250 nm and 400 nm with corresponding FWHMs of 0.220° and 0.315°, respectively.

FIG. 2(f) shows transmission spectra 260 at a wavelength of 1550 nm with void diameters of 250 nm (264) and 400 nm (262) with corresponding FWHMs of 0.220° and 0.315°, respectively. These two void sizes can be obtained from the same sample by stripping the original gold layer and then depositing another layer of a different thickness onto the same SU-8 photoresist array. The strong correlation between the linewidth and the void size verifies that the linewidth can be controlled by varying the void size via the gold film thickness with this oblique sputtering technique, as shown in FIG. 2(e).

Figure 2G:
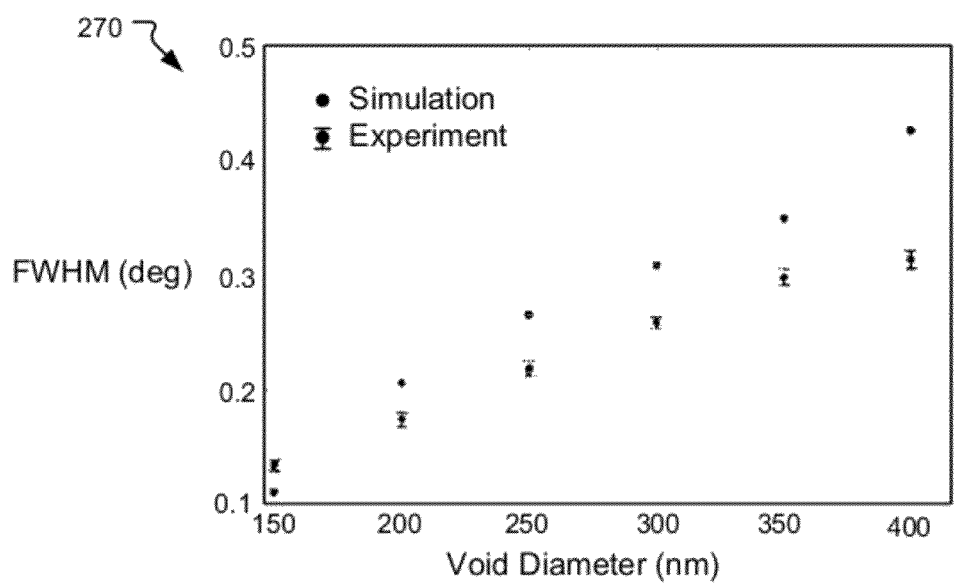
FIG. 2(g) shows a comparison of the angular FWHM vs. the void diameter for both simulation and experimental data.

FIG. 2(g) shows a comparison 270 of the angular FWHM vs. the void diameter for both simulation 272 and experimental 274 data. The measurements correspond reasonably well to RCWA simulations with a small discrepancy due to the effects of directly transmitted background, which were included in the simulation but suppressed in the experiment by a polarizer analyzer arrangement. For void diameters of 150, 200, 250, 300, 350, and 400 nm, the corresponding FWHMs are 0.135°, 0.175°, 0.220°, 0.260°, 0.300°, and 0.315°, respectively.

Figure 3:
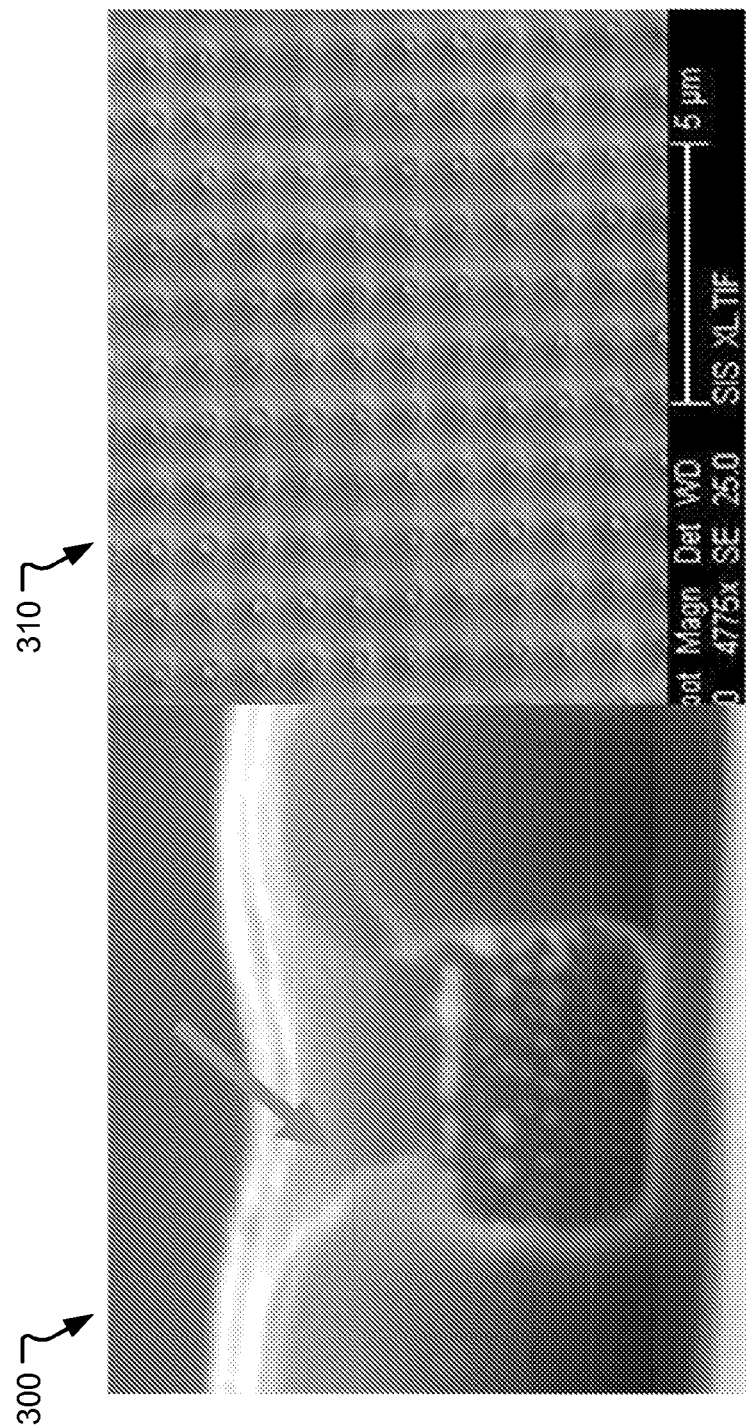
FIG. 3 shows examples of the real nanostructures for verification of the proposed approach and nanostructures by showing scanning electron-beam microscope photographs of fabricated mushroom-like structure using the processing described in FIGS. 2a-g.

FIG. 3 shows examples of the real nanostructures for verification of the proposed approach and nanostructures by showing scanning electron-beam microscope photographs 300 and 310 of fabricated mushroom-like structure using the processing described in FIGS. 2a-g. The photograph 300 on the left-hand side is a cross-section of the array, depicting the mushroomlike shape of the gold that was deposited as it protrudes out over the resist pillars as pointed by the arrow. The right-hand side photograph 310 reveals that the voids have been sealed due to overdeposition.

Preliminary tests conducted for fabrication of the 3-D composite mushroom-like metallodielectric nanostructures (see FIG. 3) show enhanced sensing capability for characterizing surface hydrophilicity and bio-recognition reaction. In the conducted tests, sensing chip is assembled by bonding fabricated 3-D composite mushroom-like metallodielectric nanostructure with PDMS chamber.

Figure 4A:
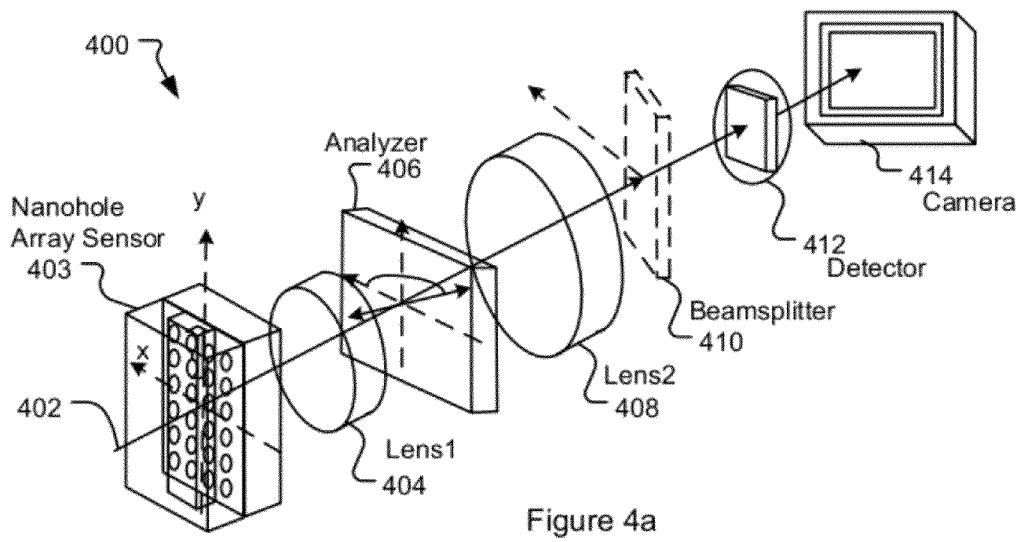
FIGS. 4a and 4b show experimental setups.
Figure 4B:
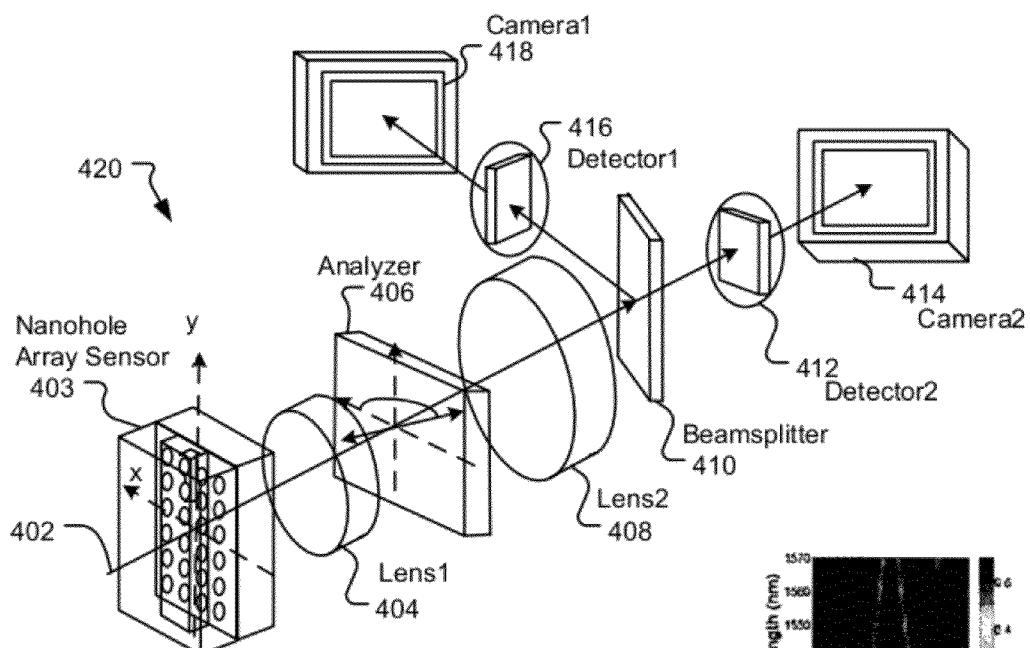

FIGS. 4(a) and 4(b) show experimental setups 400 and 420. Polarized laser beam illuminates the sensing chip 403 (e.g., an assembled 3-D composite mushroom-like metallodielectric nanostructure chip with polydimethylsiloxane (PDMS) microfluidic chamber) to excite SPP and couples to LSPP, and the transmitted resonant signal is filtered by the crossed polarized-analyzer pair 406 and imaged to CCD cameras 414, 418 and detector 416 by a 4f imaging system 404 and 408. For example, a PDMS chamber with six 2000×100× 50 μm³ channels with 100-μm separation wall was fabricated using the standard soft lithography; then bonded to the composite nanostructure by applying oxygen plasma bonding with either the substrate SiO₂ edge or with the PDMS channel wall surface deposited with SiO₂ thin film in order to overcome the poor adhesion between PDMS and Au surface.

The setup in FIG. 4(a) includes a 4-f imaging system (e.g., lens 1 (404) and lens 2 (408)), a crossed analyzer 406, photodetectors 412, and a CCD camera 414. The angular spectrum of the water-metal SPP wave excited by the 1.2 μm hole array sensor in the assembled 3-D composite mushroom-like metallodielectric nanostructure chip 403 with water filled in the channel can be measured. Additionally the set up can include a beamsplitter 410 to split the laser beam towards additional detector 416 and additional camera 418 as shown in FIG. 4(b).

In operation, tubes connected with needles can be inserted into the ports of the PDMS channel for on-chip optofluidic measurement. The assembled device can be mounted on a rotation stage, where multiple channels can be connected with tubes. Additionally, the setup layout can include a microfluidic delivery system, which includes a microcontrolled pump (e.g., VICI Valco Instruments) with adjustable flow rate and a mechanics to control the flow rate using height adjustable syringe tubes. As shown in the optical setup illustrated in FIGS. 4(a) and 4(b), the assembled chip 403 is illuminated by a polarized beam. The directly transmitted background is filtered out by an analyzer 406, and the plasmonic resonant signal can be obtained by using either CCD cameras or photodetectors.

Figure 4C:
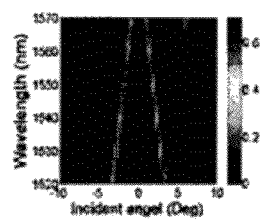
FIG. 4c shows the angular spectra of the nanoresonant array.

After mounting the sensor chip 403, the angular spectrum can be first performed by scanning both the wavelength and the angle to acquire the dispersion relationship for the WM SPP mode by filling the channel with water. FIG. 4(*c*) shows the angular spectrum of nanoresonant array sensor with water inside the channel. For the periodicity of 1.2 pm, the incident angle is 2 to 4 degree in the wavelength range of 1520-1570 nm. The incident angle was set to be 3 degree to excite the WM (1, 0) mode with a resonant wavelength around 1536 nm.

Figure 5A:
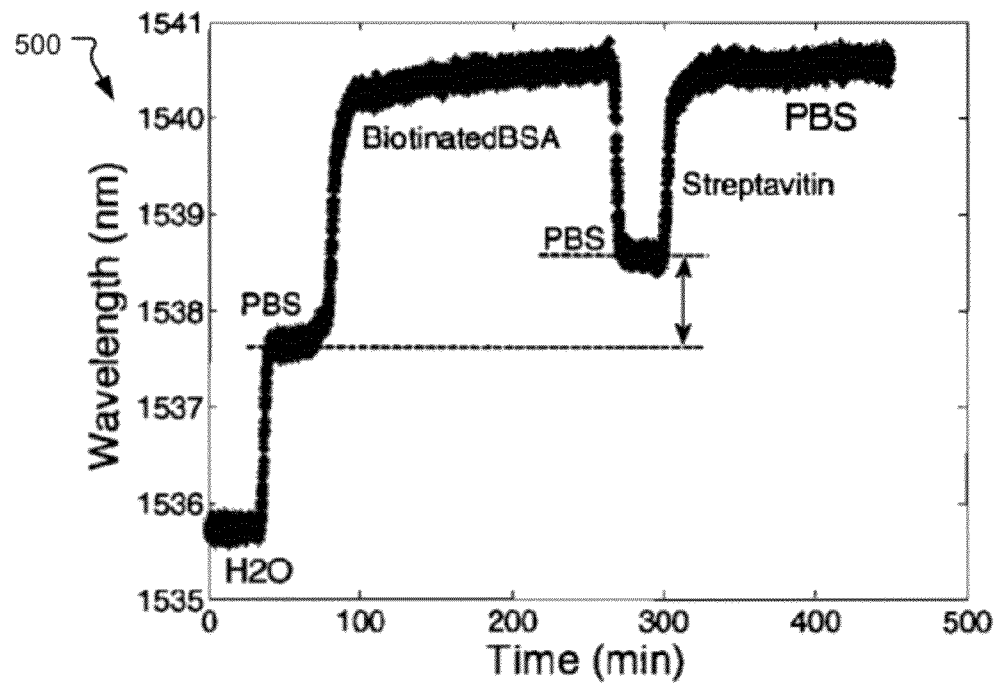
FIG. 5(a) is a chart showing resonant wavelength versus time in the real-time detection from water rinsing to PBS baseline; then immobilization of biotinylated BSA followed by PBS rinse; streptavidin binding and finally PBS washing.
Figure 5B:
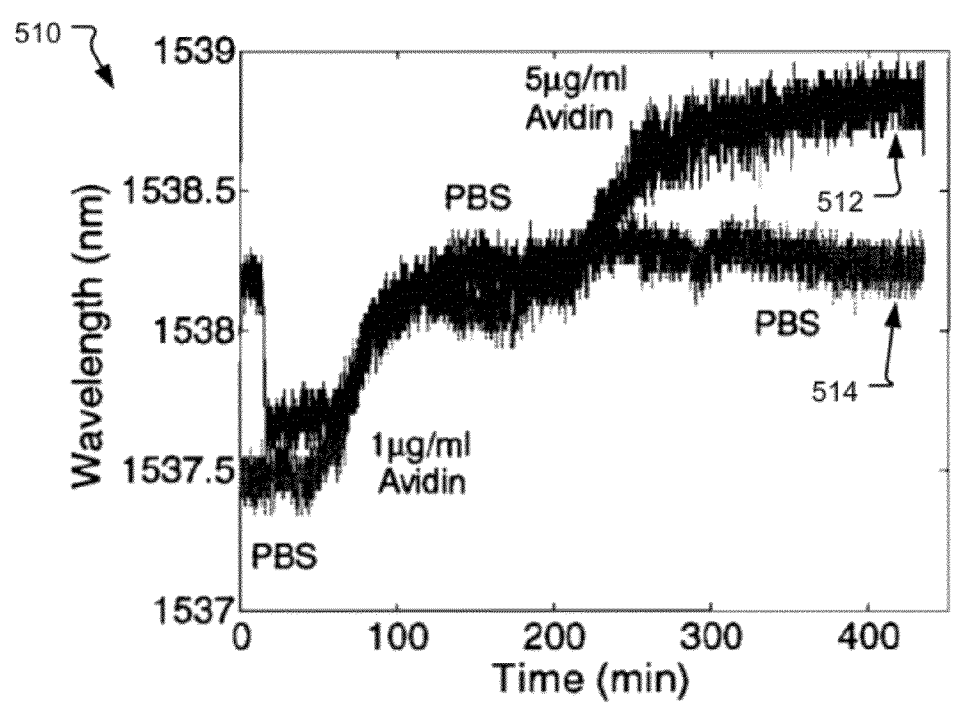
FIG. 5(b) shows that the reference channel of pure gold surface could not be used as a control.

FIG. 5(*a*) is a chart 500 showing resonant wavelength versus time in the real-time detection from water rinsing to PBS baseline; then immobilization of biotinylated BSA followed by PBS rinse; streptavidin binding and finally PBS washing. The curves in FIG. 5(*a*) correspond to two individual channels monitored simultaneously in real-time and shows the consistency between multiple channels. Two curves of the two channels are virtually indistinguishable.

Data recoding started when water first flowed into the two channels. The resonant wavelength was set to 1535.7 nm by rotating the sensor chip ~3 degree from its normal. The flow rate was set to be 16 μm/min. After 30 min, phosphate buffered saline (PBS, Invitrogen) was introduced into the two channels, and the resonant wavelength shifted to 1537.7 nm, which was the base line for the sensing configuration. After PBS flowed for 30 min, 0.2 mg/ml biotinylated bovine serum albumin (BSA, Sigma-Aldrich) in PBS with 1% 2-mercaptoethanol (Sigma-Aldrich) was introduced into the channels, the resonant wavelength shift caused by BSA was different from the shift for water and PBS, which was caused by the only bulk refractive index change. The shifts caused by the BSA solution resulted from two factors: bulk refractive index change from the concentration change, surface refractive index variation resulting from the immobilization of biotinylated BSA on the gold surface. The latter can be visualized as the slow and gradual increase of the resonant wavelength due to the slow binding reactions of thiol groups in biotinylated BSA molecules to the Au surface. It can be seen from FIG. 5(*a*) that the surface refractive index increases, i.e., the immobilization of biotinylated BSA, still continues after more than two hours. After PBS washing for about 40 min, the shift is 0.8 nm, corresponding to about 1.0 nm of biotinylated BSA immobilized on Au surface. Then, 0.1 mg/ml of streptavidin (Sigma-Aldrich) was added to bind to the immobilized biotinylated BSA for 56 min, followed by PBS washing. It can be concluded that the biotin-avidin binding reaction is quite fast, which, of course, is also concentration depended. Its binding affinity is so strong that even PBS washing could not bring any discernible binding reduction. In FIG. 5(*a*), the curves correspond to two different channels monitored simultaneously. The resonant shifts are almost identical for the two channels except for a slight red shift for the 'red' channel. This consistent response between the two channels proves the capability for multiple channel detection in the current configuration. The shifts among different channels can sometimes be pronounced because of bias difference due to fabrication processing, immobilization of biomolecules, which, however, can be removed by using data analysis and would not affect the measurement accuracy.

In order to determine the limit of detection of the proposed composite nanoresonant SPR sensor, the concentration of streptavidin should be decreased to a lower lever. A reference control should also be addressed to eliminate unwanted environmental variations by introducing two channels, one as the signal channel and, the other, as the reference channel for cancellation of environmental fluctuations.

In another implementation, a fresh sensor chip was assembled, and two of the six channels were filled with PBS to check the flow rate. Then, 0.1 mg/ml of biotinylated BSA was introduced into one channel for more than 2 hours with flow rate of about 24 μg/min, while keep flowing PBS in the other channel. In this manner, the Au surface in the one channel, referred as the signal channel, was attached with biotinylated BSA, while the other one, or the reference channel, stayed unfunctionalized. Subsequently, the same solutions flowed through both channels, starting with PBS and real-time monitoring began as shown in FIG. 5(*b*). The two curves correspond to signal 512 and reference 514 channel, respectively. After PBS rinsing, 1 μg/ml streptavidin, PBS, 5 μg/ml streptavidin and PBS were introduced into the two channels consecutively. Besides the same reaction behavior as seen in FIG. 5(*a*), the higher concentration of streptavidin continued to bind with immobilized biotin whose binding strength saturated under a lower concentration of streptavidin. The shift in the resonant wavelength for 1 μg/ml of strepavidin is about 0.6 nm. Flowing 5 μg/ml of strepavidin sequentially contributed an additional 0.5 nm resonant shift. The reaction in the reference channel behaved quite differently. The resonant shift following 1 μg/ml of streptavidin injection indicated the nonspecific binding with Au surface. After it saturated with the lower concentration, the higher concentrated strepavidin could not bind onto the Au surface anymore. Furthermore, PBS rinsing washed away some bound strepavidin, as clearly shown in the final portion of the reference curve 514.

FIG. 5(*b*) also reveals that the reference channel of pure gold surface could not be used as a control. The streptavidin molecules can easily bind to the Au surface for nonspecific binding. Next, experiment was designed to block the nonspecific binding in the reference channel in order to extract only the specific binding and eliminate environmental vibrations. Moreover, the temperature of the assembled sensor chip was raised and restored to investigate the temperature influence on the immobilization of biomolecules and the binding affinity for environmental control and possible applications at high temperature environment. After a fresh sensor chip was assembled, the signal and reference channel were simultaneously filled with biotinylated BSA and BSA, respectively, with the same concentration of 50 μg/ml for more than 2 hours. Then, 50 μg/ml of BSA solution was introduced into both channels for twenty minutes to cover any possible bare Au surface, blocking any possible streptavidin nonspecific binding. Both channels were then washed with PBS and real-time monitoring began as shown in the chart 600 in FIG. 6(*a*). The two curves correspond to the reference 606 and the signal 608 channels, respectively, which exhibit 0.6 nm resonant bias. The sensor chip was mounted on a custom ordered thermo-electric cooler (TEC) module. The central part in the TEC was removed and the substrate of the sensor chip was sitting on the edges of the TEC module. First, the temperature was set at a room temperature of 23.5° C. After about 40 min, the temperature was raised to 55° C., and then set back to 23.5° C. The change in environmental temperature can be clearly viewed in the real-time detection as shown in FIG. 6(*a*). When the temperature increased, the resonant response dropped rapidly. After the temperature was reset back to 23.5° C., the resonant response restored slowly.

At about 140 min, the resonant response had already shown very slow change, 50 ng/ml of streptavidin was then introduced into both channels. The resonant shift in the signal channel started increasing relatively quickly, while the reference channel exhibited constantly slow increment. After about 60 min, PBS was added into both channels for about 30 min, then 500 ng/ml of streptavidin was added into both channels for additional binding test. The resonant response in the signal channel 608 started to shift more quickly until it saturated, while the reference channel 606 maintained the same pace. Finally PBS was filled into both channels, washing the unbound streptavidin in both channels. In order to clearly see the reactions in the reference 606 and signal 608 channels, the bias between the two channels was removed by shifting the reference channel response −0.6 nm, which gives the shifted reference curve 610. Compared with the shifted reference curve 610, the specific binding in the signal channel can now be seen more clearly. Comparing the shifted reference curve 610 and the signal curve 608, the two curves almost overlap before the introduction of streptavidin, except for the rapid temperature change as indicated by the dotted box 604 in FIG. 6(a). The difference in the resonant response in the box 604 indicated the non-uniform temperature distribution in the two channels, which resulted from the relative position difference of the two channels on the TEC module and could be resolved by prolonging the heating or cooling cycle for uniform heat distribution. The ripples on the two curves came from the rapid pressure shift in the pump system. The consistency of these ripples in two curves confirmed them to be systemic error. When the temperature of sensor chip slowly reached room temperature, the two curves (blue and green) overlapped again. As seen in the inset 602, which is a zoom-in view of the signal curve 608 and the shifted reference curve 610 after reaching room temperature, the slow evolution of the reference curve points to the possible nonspecific and temperature drift in both channels.

Figure 6A:
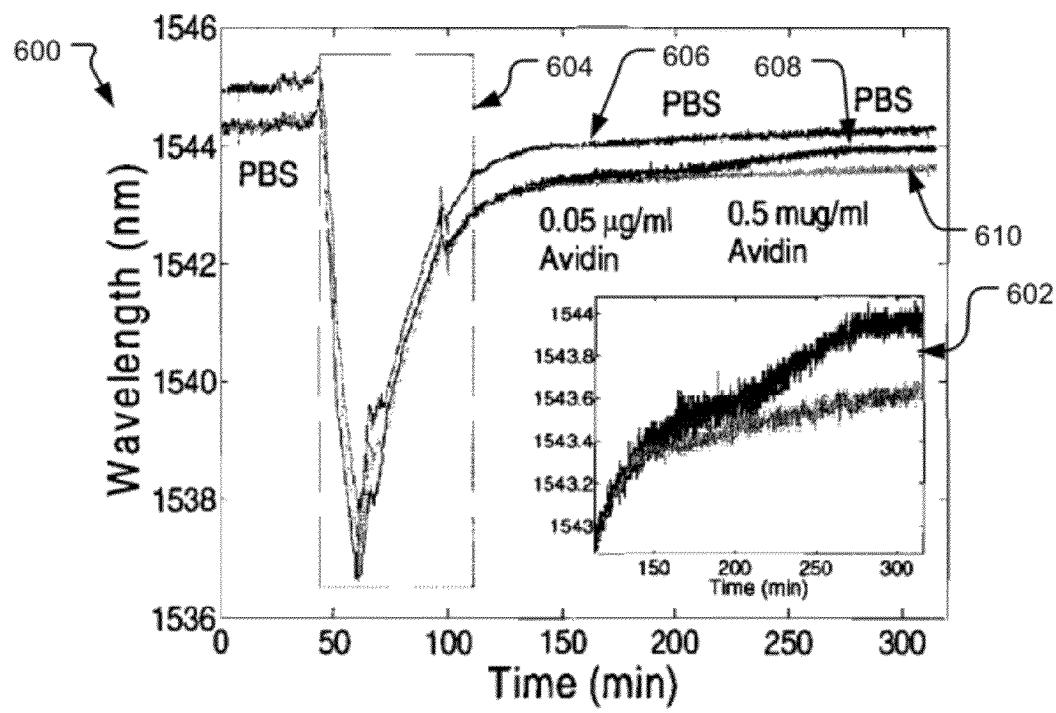
FIG. 6(a) shows real-time monitoring of a sensor chip.
Figure 6B:
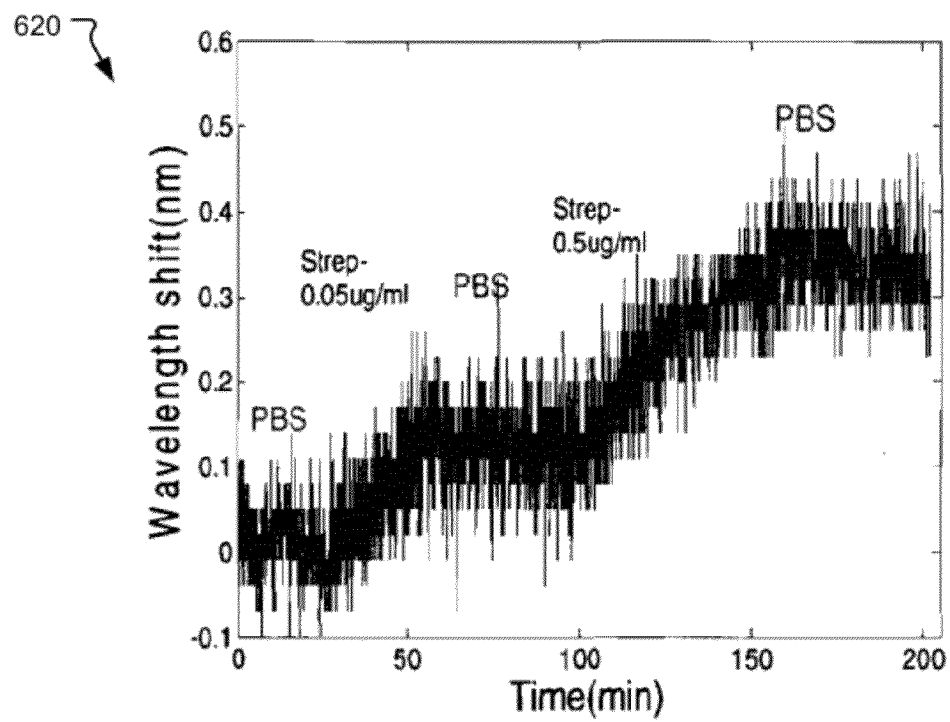
FIG. 6(b) shows that environmental influences can be eliminated by subtracting the reference response from the signal channel.

The above described environmental influences can be eliminated by subtracting the reference response from the signal channel as shown in the chart 620 of FIG. 6(b), whose origin was reset. FIG. 6(b) clearly shows the different reaction stages from PBS base line, 50 ng/ml streptavidin binding, PBS washing, 500 ng/ml streptavidin binding, and final PBS washing. The 50 ng/ml streptavidin binding gives 0.13 nm resonant shift. Considering the standard deviation of 15 pm of the current setup, which is obtained by monitoring the resonant drift of DI water, and 3 times the standard deviation estimation, the limit of detection would be 17 ng/ml (0.3 nM), which is much lower than regular nanohole array sensor of 3 µg/ml (26 nM).

As evident from FIGS. 6(a) and 6(b), both the resonant responses of reference and signal channel shifted by about 1 nm after they recovered from the temperature change. This could have resulted from a loose screw due to temperature cycling, which could have rotated the sample slightly. Another possible reason, or partial shift, maybe due to the disassociation of immobilized biotinylated BSA and BSA C are fully designed experiment can be used to address these issues. Nevertheless, these shifts did not affect the final experimental result because these factors occurred in both channels and can be eliminated to obtain only the specific binding events by subtracting the reference response from the signal channel. The rapid resonant shift within the temperature variation, as shown in FIG. 6(a), also provides a new tool to measure the temperature derivative of the refractive index of liquid, which is about $2.0 \times 10^{-4}$ $(k^{-1})$ for the PBS solution from the evaluation of the sensitivity and the resonant wavelength shift.

Additionally, the fabricated composite nanostructure array can be used to determine the surface hydrophilicity by measuring the resonant wavelength shift in the laser beam transmitted through the 3D nanostructure array, which is bonded to a polydimethylsiloxane (PDMS) chamber. Only the AM mode was monitored because the required wavelength to excite the liquid-metal mode is outside of the laser's range. The surface properties of a clean unfunctionalized gold surface were investigated. Using a computercontrolled acquisition system, a baseline was established for the resonant wavelength of an air-filled PDMS chamber.

Figure 7A:
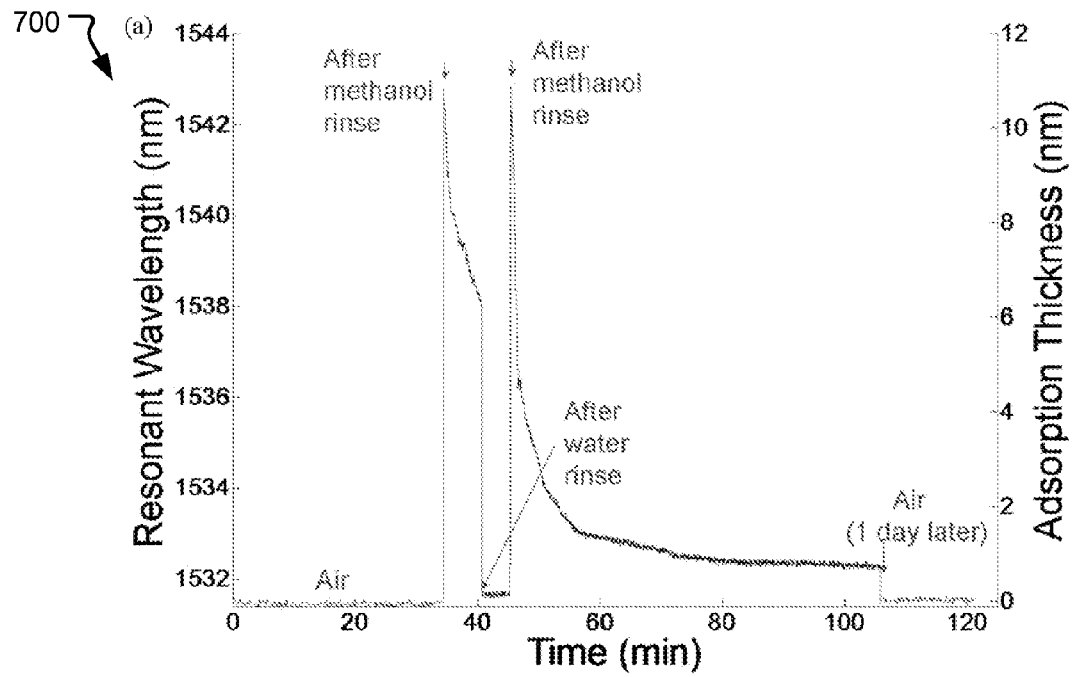
FIG. 7(a) is a chart that shows measured real-time resonant wavelength shifts and the calculated adsorption thicknesses by the assembled 3-D composite mushroom-like metallodielectric nanostructure SPR sensor integrated with a PDMS channel for aqueous delivery of water and methanol to verify the hydrophilicity property of Au surface as hydrophobic for water molecules and hydrophilic for methanol molecules.

FIG. 7(a) is a chart 700 that shows measured real-time resonant wavelength shifts and the calculated adsorption thicknesses by the assembled 3-D composite mushroom-like metallodielectric nanostructure SPR sensor integrated with a PDMS channel for aqueous delivery of water and methanol to verify the hydrophilicity property of Au surface as hydrophobic for water molecules and hydrophilic for methanol molecules. Surface hydrophilicity was characterized by accurately monitoring the adsorbed liquid layer after rinsing the nanostructure surface. Methanol and water were injected into the PDMS chamber serially and acquisitions started once all the liquid had flown over the gold surface and out of the 200 µm-wide PDMS channel. By relating the adsorption thickness to the resonant wavelength shift, the dynamic adsorption thickness can be calculated and plotted on the right side of FIG. 7(a). After the initial methanol rinse, the adsorption thickness decreases from 10.7 nm to 6.3 nm over a 6.2-minute span. After water rinsing, however, the resonant wavelength shift is instantaneous with a relatively constant adsorption thickness of 0.2 nm over a 5.8-minute span. The data indicates that a clean, unfunctionalized gold surface is hydrophilic to methanol but hydrophobic to water molecules. Experiment was also conducted to confirm the hydrophilicity change after functionalizing the gold surface.

In order to modify the surface properties, 3-mercaptopropyl-trimethoxysilane was injected into the PDMS chamber and the chemical solution evaporated overnight. This produced a self-assembled monolayer (SAM) on the gold surface, as evident by the increasing absorption thickness as shown in the chart 710 of FIG. 7(b). A similar procedure was conducted to determine the hydrophilicity of the Au-SAM surface to water and methanol molecules. The adsorption thickness after water rinsing was 22.7 nm, with no significant change over a 10-minute span. After methanol rinsing, however, the adsorption thickness decreases to only 2.0 nm.

Figure 7B:
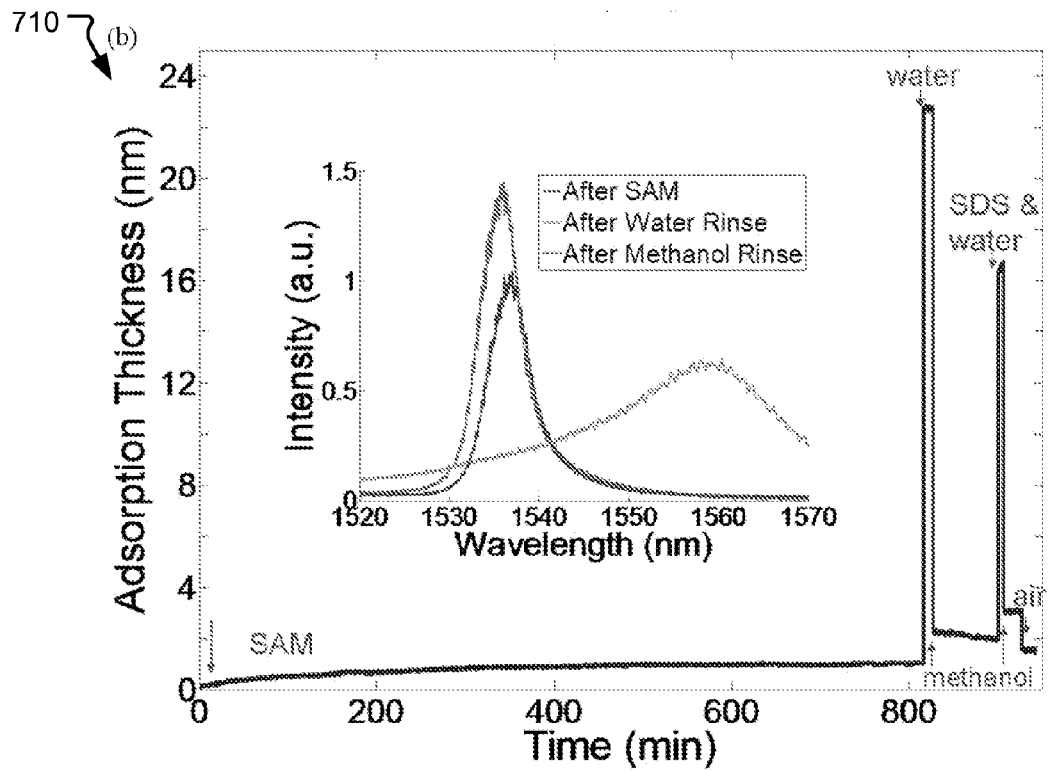
FIG. 7(b) shows the calculated absorption thickness.

The calculated adsorption thickness in FIG. 7(b) shows that the SAM has modified the hydrophilicity property for water molecules from hydrophobic to hydrophilic and methanol molecules from hydrophilic to hydrophobic. For example, the adsorption thickness increases from 0.2 to 22.7 nm, which reveals that the SAM layer had modified the surface from hydrophobic to hydrophilic for water. The modified surface, however, resists the wetting by methanol where the adsorption thickness drops to 2.0 from 10.7 nm for the unmodified Au surface. In FIG. 7(b), the decaying behavior is not observed after water rinsing within the measurement time due to water's low vapor pressure in the chamber. Similar behavior occurs when the sensor was rinsed with a solution of 2% sodium dodecyl sulfate. The insets in FIG. 7(b) show three spectra measured after SAM binding, water rinsing, and methanol rinsing.

Measurements obtained in these preliminary tests have demonstrated the much better sensing capability of the proposed 3-D composite nanostructure than that of the nanohole-only array sensing configuration. Also, various devices that support both surface plasmonic resonances, the propagating surface plasmon polariton (SPP) waves and localized surface plasmon resonant (LSPR) modes, and the associated techniques for sensing have been described.

As described above, a composite mushroomlike metallodielectric nanostructure can be implemented to enhance the normal electric field by coupling between localized plasmons and propagating SPPs. Optimized design employing LSPR coupling to propagating SPP modes and multiple SPP mode couplings can also be implemented. The fabrication method described herein is a low cost and mass-producible technique to construct 3D composite nanostructures in which samples are reusable and reconfigurable. Tradeoffs between FWHM linewidth and deposition thickness, in terms of its effect on the transmission intensity, can create an optimized design in yielding the best resolution for the SPR sensor. Moreover, other SAM materials can also be used in order to engineer the material's surface properties for applications in biosensing, such as detection of protein interactions on the gold surface. Current ongoing investigations of antibody-antigen interactions using these SPR composite nanostructures are promising.

Additionally, a composite nanoresonant structure with nanovoids in metallic film has been described and demonstrated to have enhanced sensitivity in biorecognition reactions. The enhancement can be realized by coupling the LSPR from the propagating SPP, resulting from the periodic perforation under the phase matching condition. The near field distribution shown and described above implicates imperfect excitation of the LSPP, an optimized design is being carried on by modifying the nanovoid geometry and using multiple SPP mode couplings. The fabrication method described herein represents a cost-effective way to build the composite nanostructures in which the chips are reusable and reconfigurable, because the metallic layer can be stripped away and a new layer redeposited to the same or different thickness. Although the reference channel concept has been described for prism-based sensing configuration, reference channel can be employed to improve the limit of detection of nanoresonant SPR sensor by taking advantage of its capability of the large amount parallel detection characteristics. Nonspecific binding can be eliminated by blocking the surface in the reference channel and extraction of the reference from the signal channel to eliminate influences from nonspecific bindings and environment vibrations. Moreover, specific binding can be verified to be still efficient after certain heating process. By using the nanoresonant, the limit of detection can be improved to sub-nM from tens of nM in conventional nano-hole array SPR sensor. Due to the strong affinity between biotin and avidin, it can be difficult to regenerate the sensor chip surface to conduct the calibration experiments. Therefore, each time a fresh sensor chip was used to conduct the binding performance, resulting in different amount of immobilization and the bias difference. Renovated prototype setup with various concentration arrangements can be built for comprehensive evaluation based on multiple spot detection using CCD camera or detector array.

In another aspect, 3-D composite metallodielectric nanoresonant array structure can be implemented to couple the SPP wave and the LSPR to achieve: (1) LSPR, or very 'hot spot' array with high localized electric field strength; and (2) the enhanced surface plasmonic propagating electric field, and reduced penetration depth, which is defined as the distance from the interface at which the amplitude of the field decreases by a factor of 1/e. The factor (2) can directly increase interaction cross-section with the detected molecules, and increases the surface sensitivity of the SPP sensing configuration.

Several sensing configurations can be applied for the above two factors including: 1) Plasmonic sensing only; 2) Raman scattering only; and 3) Plamonic sensing+Raman scattering simultaneously. For example, the plasmonic sensing configuration can include propagating surface Plasmon polariton (SPP) sensing configuration. Using enhanced surface electric field and micro-channel configuration, the molecule in interest can be sensed for average interaction effect within certain surface area (e.g., ~100 micron in diameter.) Also, plasmonic sensing configuration can include LSPR sensing that monitor the location, or locations of the nanoresonators (voids), to detect the molecules near the voids. The LSPR signals are not susceptible to the environmental (temperature) because of the localized electric field within only the void area. Also, through-hole fluidic configuration can be applied to detect small molecules.

The Raman scattering only configuration can include using generated 'hot spot' array for Raman detection to directly identify the molecules. The Raman scattering only configuration can include a passing-through configuration. The through-hole fluidic configuration includes top and bottom fluidic channels, and can be used to let the small molecule (<20 nm) passing though the void, so that the molecule senses the maximal local electric field, experience the maximal interaction, and yield maximal enhancement Raman detection. A micro-channel(s) can be used to deliver molecules through many voids for multiple detections. Micro or nanochannel(s) can be used to deliver molecule into specific void for single detection.

The Raman scattering only configuration can also include a pass-over configuration. This configuration only has one micro fluidic channel over the 3-D composite metallodielectric nanoresonant array. When the molecules in interest pass over the voids, due to the interaction with the local electric field, Raman scattering occurs and a signature signal can be detected to identify the molecules. This configuration can be used to detect both small and big molecules.

The configuration that combines Plamonic sensing and Raman scattering simultaneously can include propagating SPP and Raman scattering. The SPP resonant shift can be monitored over a certain area on the 3-D array surface for the quantity information of the molecules in interest on the surface. At the same time, the configuration can include monitoring the Raman scattering from the voids (3D nanoresonators) simultaneously for fast identification of the molecules. The passing-through fluidic configuration can be used for small molecule, and the pass-over fluidic configuration can be used for both small and large molecules.

The configuration that combines Plamonic sensing and Raman scattering simultaneously can include LSPR and Raman scattering. The LSPR resonant shift over a single or multiple 3-D voids can be monitored to obtain the quantity information of the molecules in interest near the voids. At the same time, the Raman scattering from the voids (3D nanoresonators) can be monitored simultaneously for fast identification of the molecules. The pass-through fluidic configuration can be used for small molecules, and the pass-over fluidic configuration can be used for both small and large molecules.

In addition to the fabrication methods described above, an on-chip in-plane integrated system can be used to fabricate a nanostructure device described herein. The on-chip in-plane integrated system uses SOI (Silicon on insulator or Silicon on Silicon Oxide) standard chip (wafer) to build a sensing device. This can improve the deployment ability. Other multiple layer wafers can also be applied using these procedures.

Figure 8:
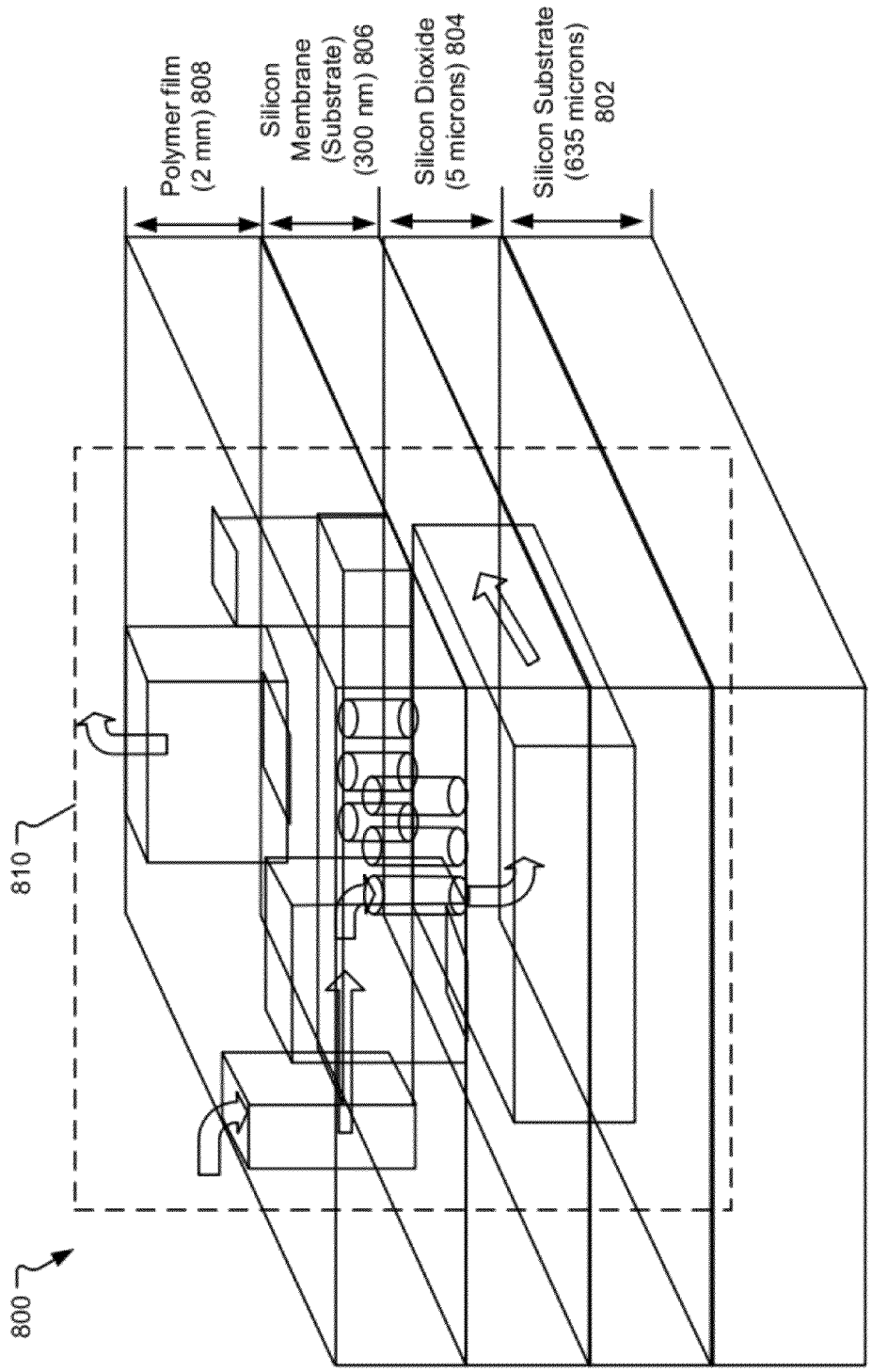
FIG. 8 is a block diagram of an example nanostructure device.

FIG. 8 is a block diagram of an example nanostructure device 800. The nanostructure device 800 includes a substrate layer (e.g. silicon) 802 with a silicon dioxide layer 804 deposited over the substrate 802. Also, a silicon membrane layer 806 is deposited over the silicon dioxide layer 804, and a polymer film layer 808 is bound over the silicon membrane layer 806. The device 800 includes integrated fluidic channel 810 with the arrows indicating direction of flow.

Figure 9:
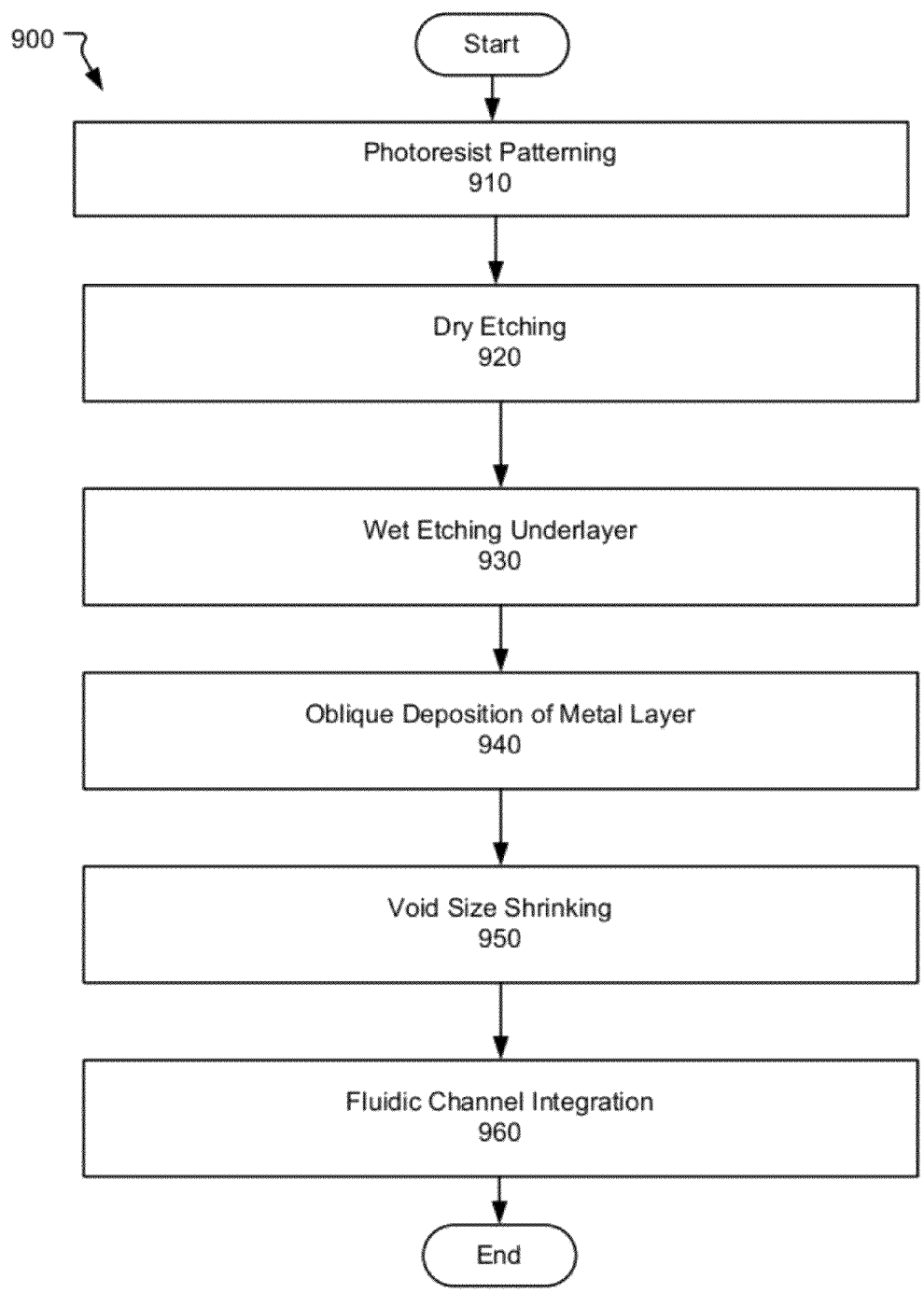
FIG. 9 is a process flow diagram of a process for fabricating a nanostructure device.

FIG. 9 is a process flow diagram of a process 900 for fabricating a nanostructure device. The fabrication process 900 includes photoresist patterning (910); dry etching (920); wet etching underlayer (930); oblique deposition of metal layer (940); void size shrinking (950); and fluidic channel integration (960).

Figure 10:
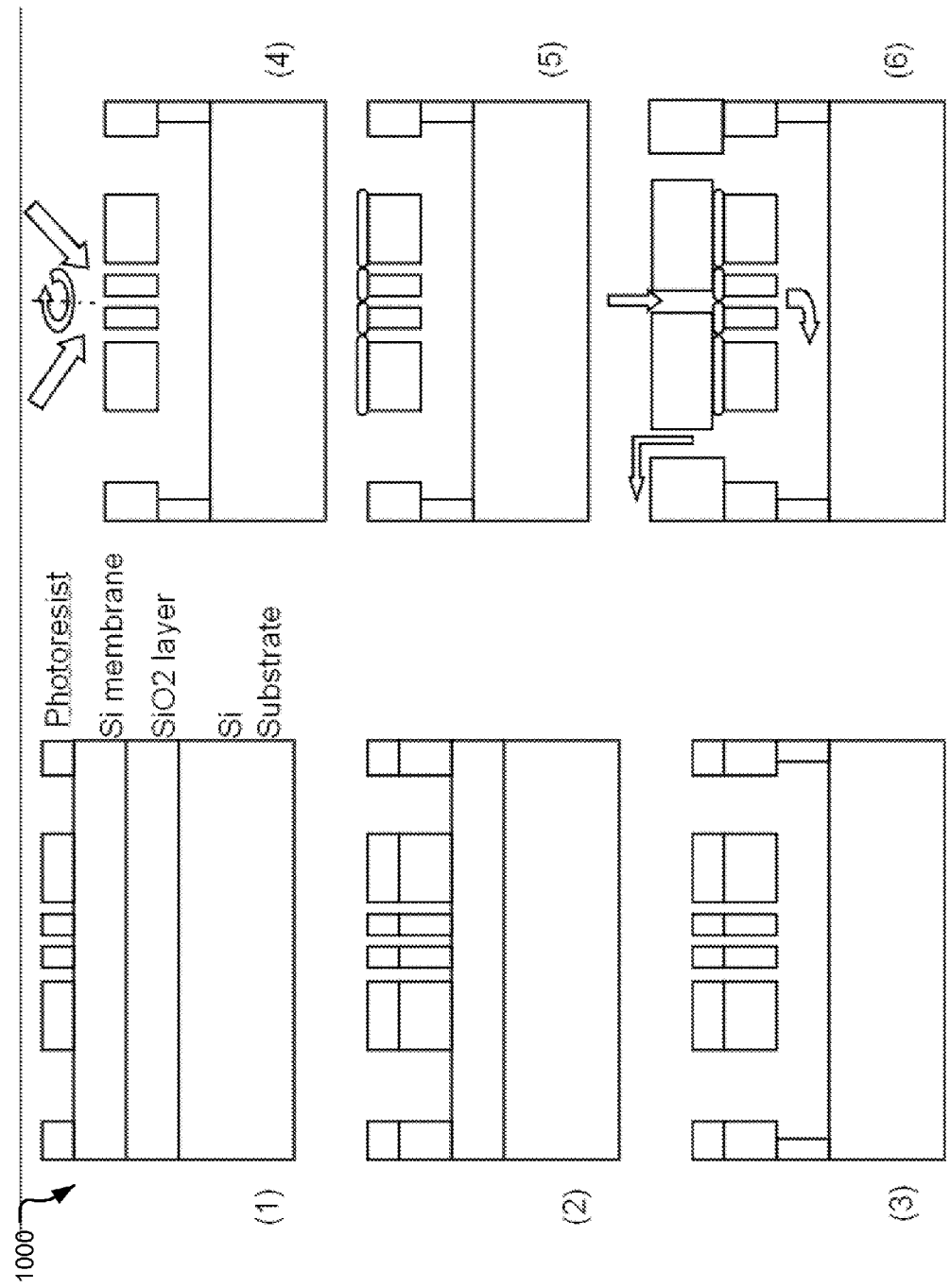
FIG. 10 is a block diagram that illustrates the fabrication process 900 of FIG. 9.

FIG. 10 is a block diagram 1000 that illustrates the fabrication process 900 of FIG. 9. Panel (1) shows a cross-sectional view of a nanostructure device with the substrate (e.g., silicon), a silicon dioxide ($SiO_2$) layer, a silicon membrane layer, and a photoresist layer. The photoresist layer is patterned as shown to generate the void structure. In panel (2), dry etching patterns the silicon membrane below the patterned photoresist layer. In panel (3), wet etching underlayer removes portions of the silicon dioxide layer to create a channel. In panel (4), oblique deposition of a metal layer (e.g., gold) on top of the silicon membrane is shown. Panel (5) shows the result of void size shrinking. Panel (6) shows fluidic channel integration.

Figure 11:
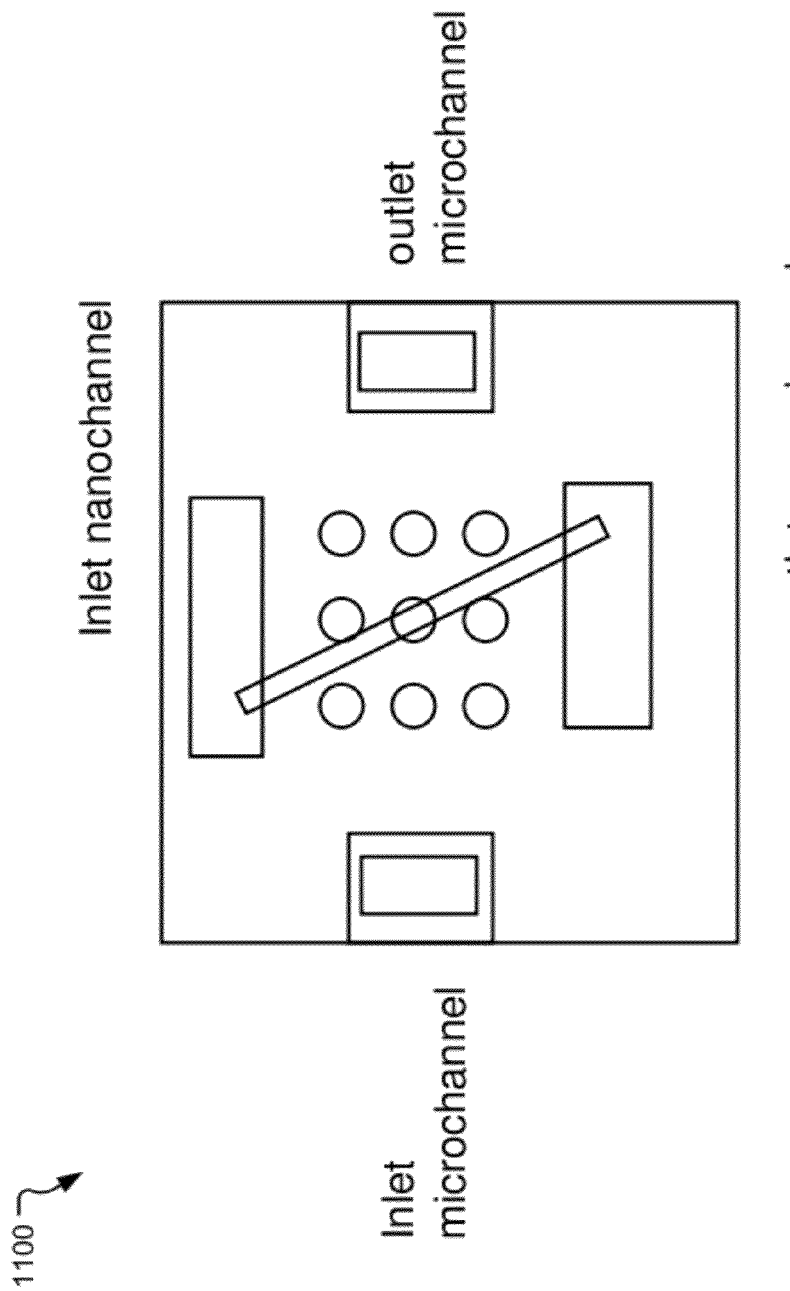
FIG. 11 is a top-down view diagram that shows the micro and nanochannels of a device.

FIG. 11 is a top-down view diagram 1100 that shows the micro and nanochannels of a device. The inlet and outlets of the nanochannel and the microchannel are clearly labeled.

Figure 12:
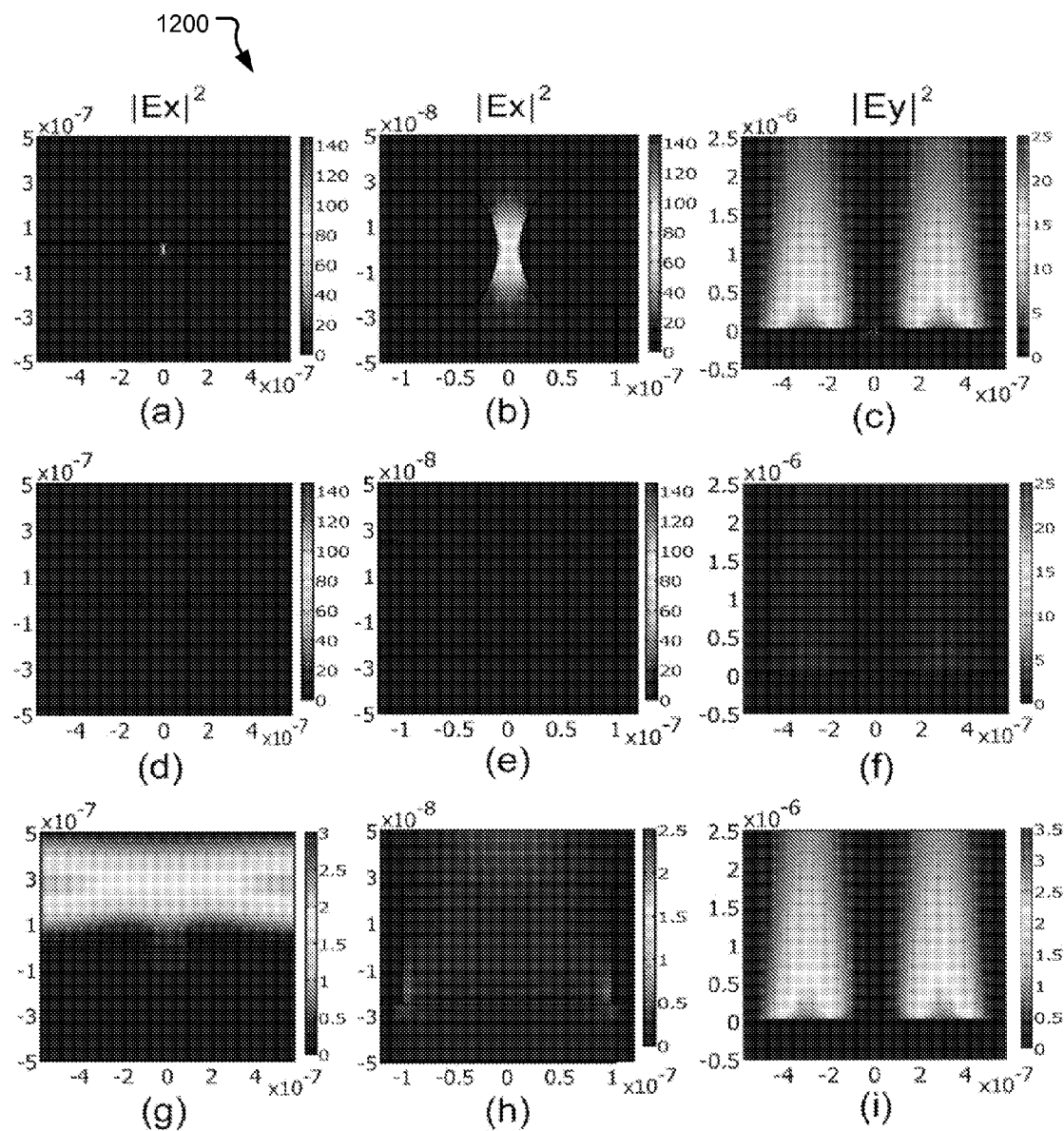
FIG. 12 shows near-field FEM simulation for simultaneous excitations of LSPR and SPP.

FIG. 12 shows near-field FEM simulation 1200 for simultaneous excitations of LSPR and SPP. FIG. 12, panels (a)-(c) show the intensity distribution of the electric field in the MMN substrate on the water-metal interface. FIG. 12, panels (d)-(f) show the intensity distribution with the same scale for a conventional nanohole structure. FIG. 12, panels (g)-(i) show the rescaled field distribution of the nanohole structure. FIG. 12, panels (a), (d) and (g) show the field intensity distribution in the x direction ( ) or along the metal surface. FIG. 12, panels (b), (e) and (h) are the close-ups of the nanoresonantor or nanohole area. FIG. 12, panels (c), (f) and (i) correspond to the field intensity in the y direction ( ) or normal to the metal surface. The units for the dimensions are meters.

Figure 13:
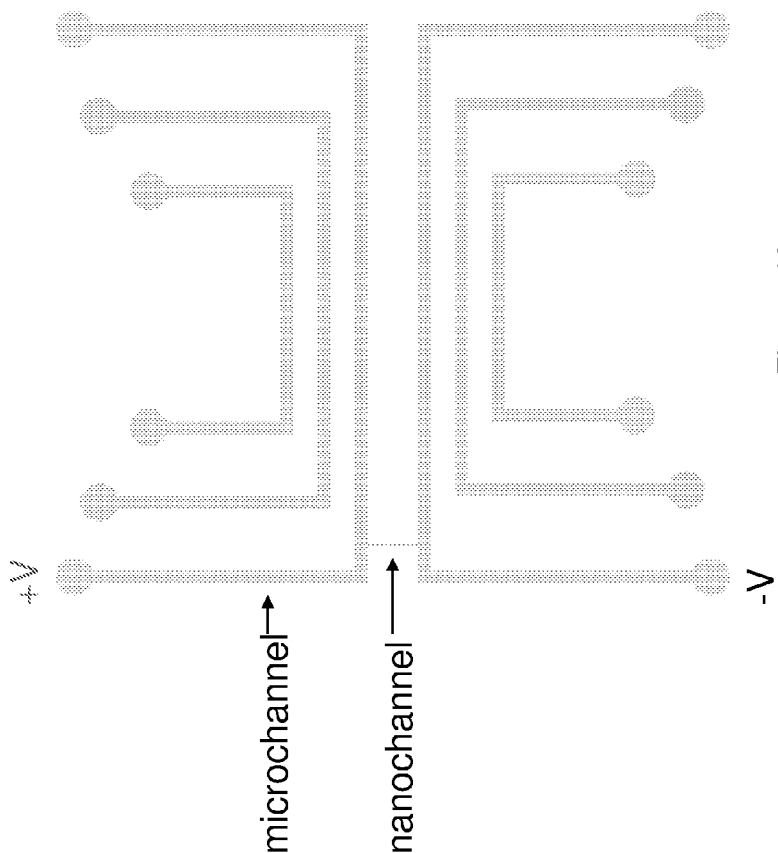
FIG. 13 shows a microchannel with nanochannel overlay.
Figure 14:
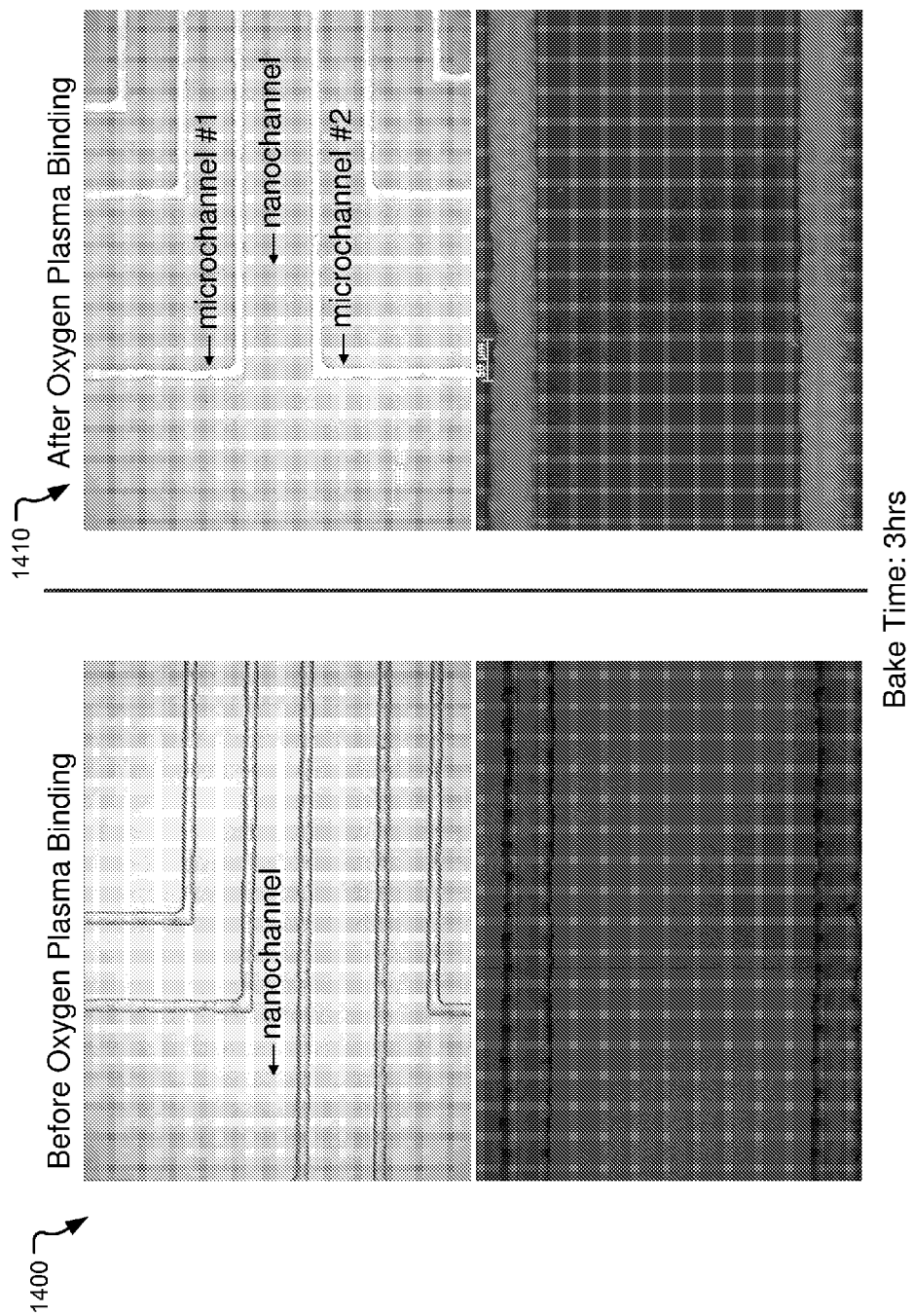
FIG. 14 shows two images that represent before and after oxygen plasma binding respectively.

FIG. 13 shows a microchannel 1300 with nanochannel overlay. FIG. 13 demonstrates a delivery system through integrated micro, nanofluidics. FIG. 14 shows two images 1400 and 1410 that represent before and after oxygen plasma binding respectively.

Figure 15:
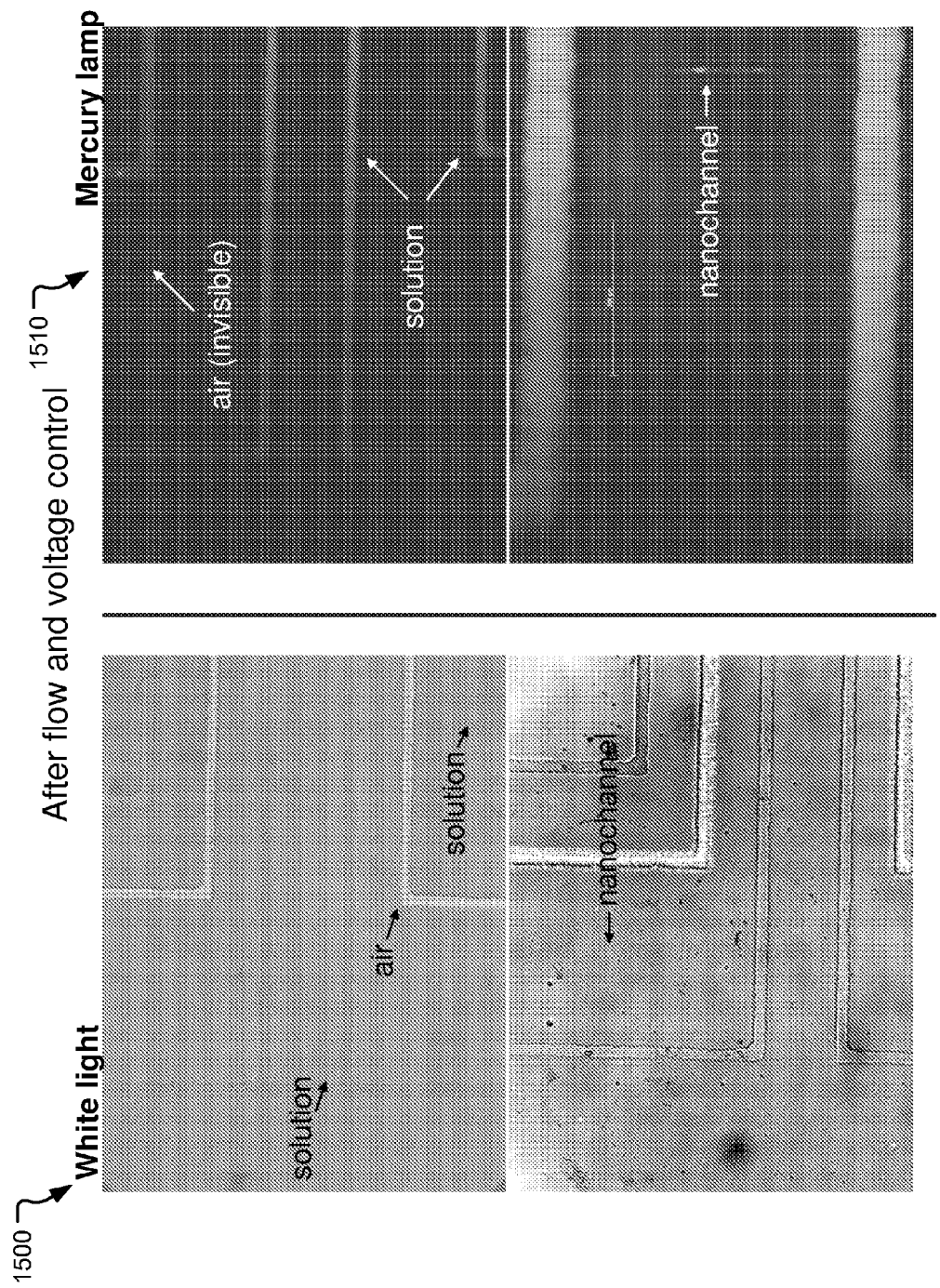
FIG. 15 shows fluorescent images that confirm flow in nanochannels.
Figure 16:
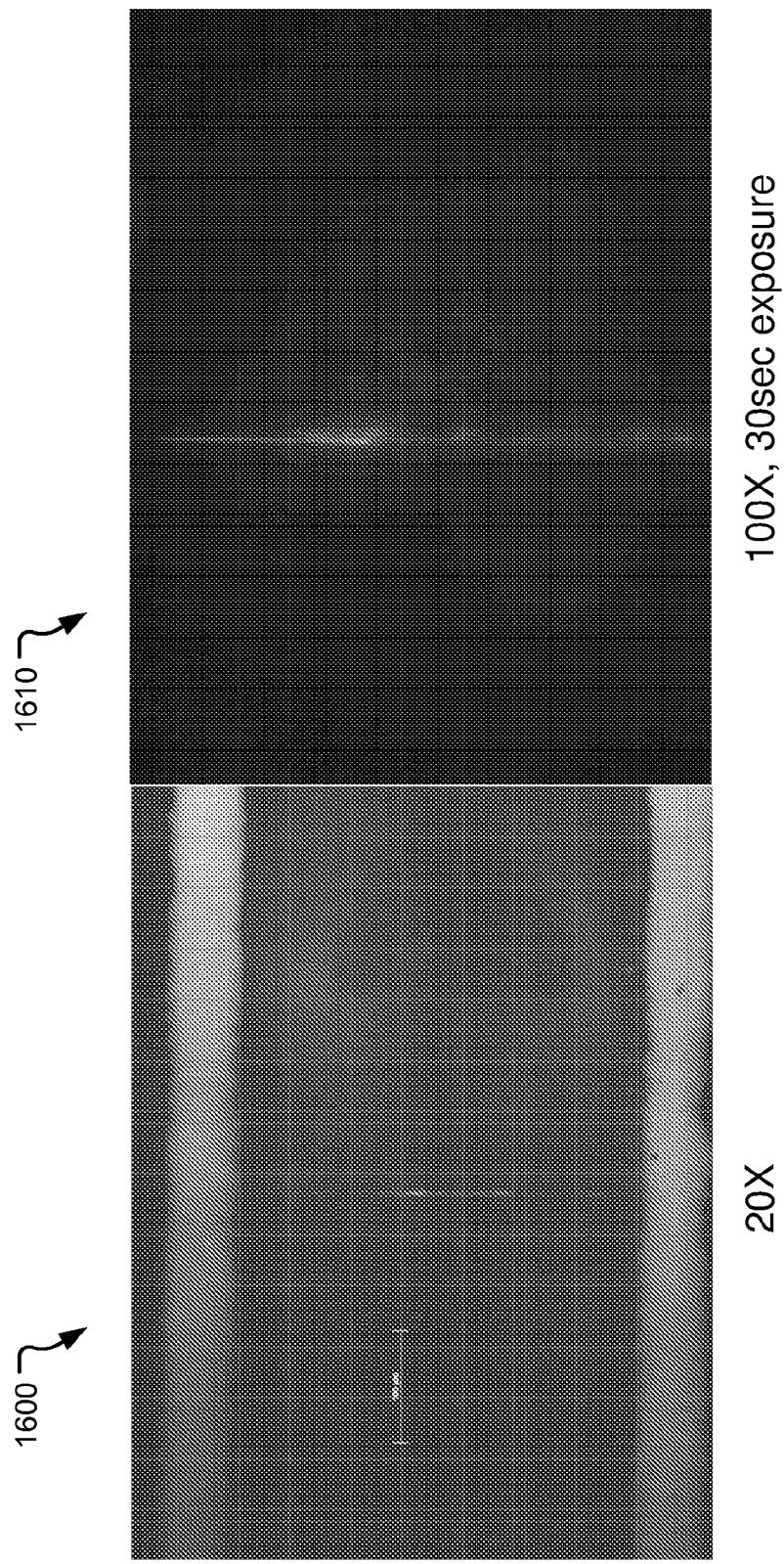
FIG. 16 shows fluorescent images of a microchannel with nanochannel overlay under 20× and 100× magnifications respectively.

Nanochannel flow experiment is shown in FIGS. 15 and 16. Testing with 40 nm fluorescent beads can be performed to visually see flow in the generated nanochannel. For example, phosphate buffered saline (PBS) solution can be flown with the beads into the 2 microchannels. Voltage can be applied across the 2 microchannels (a nanochannel connects these two microchannels). FIG. 15 shows fluorescent images 1500 and 1510 that confirm flow in nanochannels. Image 1500 shows the flow in nanochannel under white light. Image 1510 shows the flow in nanochannel under mercury lamp. FIG. 16 shows fluorescent images 1600, 1610 of the microchannel with nanochannel overlay under 20× and 100× magnifications respectively.

Figure 17:
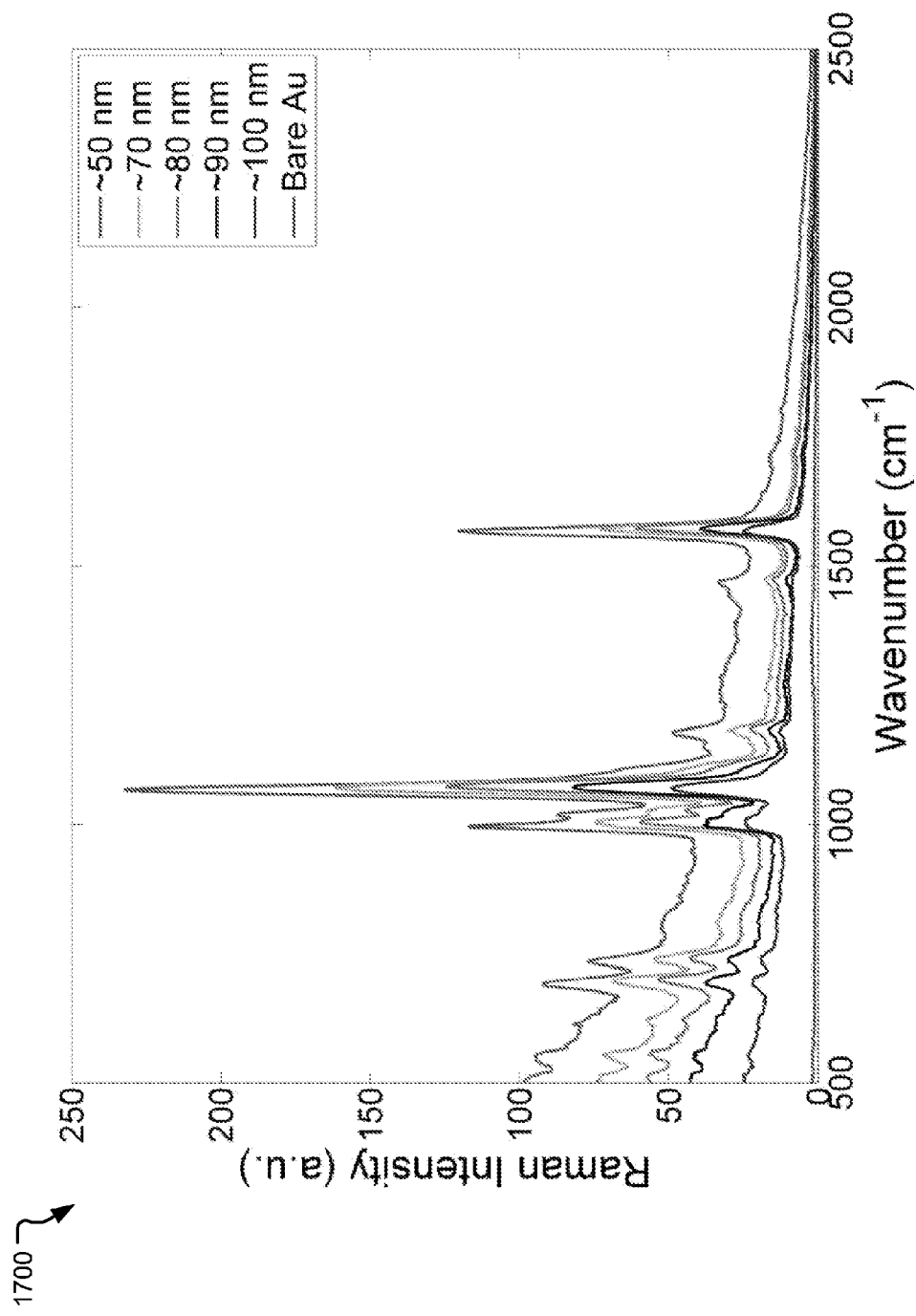
FIG. 17 shows the relationship between the Raman Intensity and Wavenumber.

FIG. 17 shows the results of near field enhancement experiment due to the dipole moment coupling. Shrinking the size of the void by oblique deposition thicker metal layer, induce the coupling strength of the dipole moment by the void, excited by the incident optical field. The increased near field electric field can be seen by the Raman signal intensity increase. FIG. 17 shows the relationship between the Raman Intensity and Wavenumber. Specifically, the increase in SERS intensity as a function of decreasing void size in quasi-3-D mushroomlike composite nanostructures is shown in FIG. 17.

The sample and the bare (unstructured) gold substrate were soaked in ~150 mM of benzenethiol in ethanol for 18 hours. The samples were then taken out and rinsed with ethanol for 3 times to wash away unbounded benzenethiol molecules. Raman measurements were then taken on the samples and reported in FIG. 17.

Figure 18A:
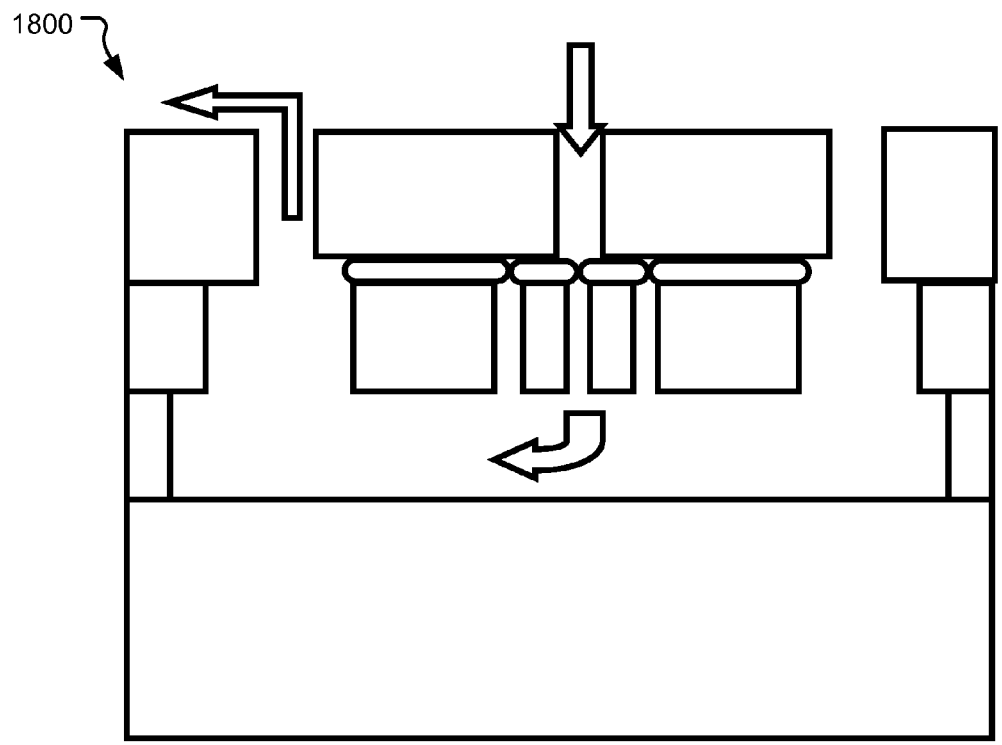
FIG. 18a show an example of the Pass Through Configuration.
Figure 18B:
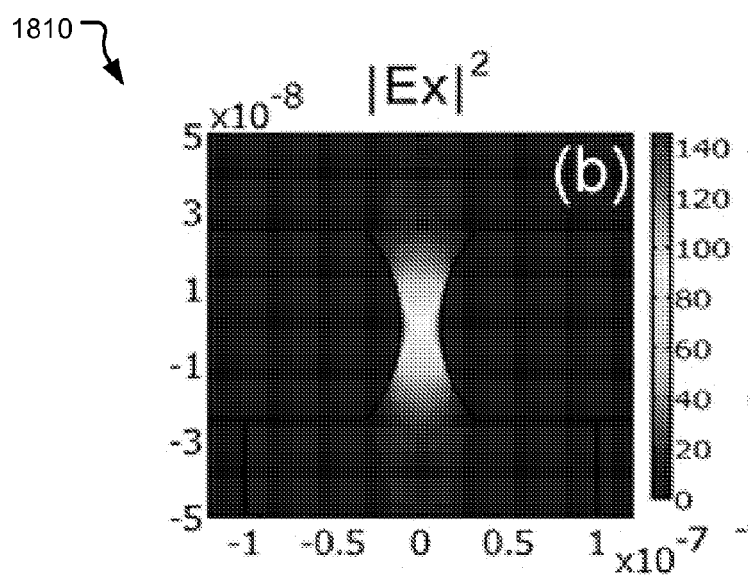
FIG. 18b shows localized surface plasmonic resonant (LSPR).

FIG. 18a show an example of the Pass-Through Configuration 1800. For small particle detection, particles of interest passing through single 3-D mushroomlike composite nanostructures experience the maximal optical field, and realize the maximal interaction cross section. Arrows show the flow of particles in the nanostructure. FIG. 18b shows localized surface plasmonic resonant (LSPR) 1810. Surface enhanced Raman signal is used for identification.

FIG. 19a shows an example of the Pass-Over Configuration 1900 used for large (micron) particle detection. Particles of interest passing over 3-D mushroomlike composite nanostructures experience the enhanced surface optical field due to the coupling between LSPR and propagating SPP (surface plasmonic polariton) wave. Arrows show the direction of particle flow. To detect the particle movement, FIGS. 19b and 19c show LSPR and enhanced SPP resonant 1910 and 1920. Surface enhanced Raman signal for identification can be used for identification.

The enhancement factor for maximum intensity along metal surface for 3-D mushroomlike composite nanostructures would be more than 100 times compared to nanohole array only. The enhancement factor for the maximum intensity for normal direction is about 7.5.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. Variations and enhancements of the disclosed implementations and other implementations can be made based on what is disclosed and illustrated.

What is claimed is:

1. A method of fabricating a nanostructure device, the method comprising:
    depositing a dielectric layer over a substrate;
    depositing a silicon membrane layer over the dielectric layer;
    depositing a photoresist layer over the membrane layer;
    patterning the photoresist layer to generate a nanohole structure comprising multiple nanoholes;
    dry etching to pattern the silicon membrane layer below the patterned photoresist layer;
    wet etching to remove portions of the dielectric layer to create a channel;
    using oblique deposition to place a metal layer on top of the nanohole structure of the photoresist layer to include openings over the nanoholes; and
    integrating a fluidic channel over the nanostructure.

2. The method of claim 1, further comprising controlling a size of the openings over the nanoholes.

3. A surface plasmon based sensing device, comprising:
a substrate;
a dielectric layer deposited over the substrate;
a silicon membrane layer deposited over the dielectric layer;
a photoresist layer deposited over the membrane layer and patterned to form a 3-dimensional composite metallodielectric nanoresonant array of nanoholes spaced from one another; and
a layer of a metallic film formed on the 3-dimensional composite metallodielectric nanoresonant array of nanoholes to include openings over the nanoholes respectively,
wherein the metal film is deposited using oblique deposition; and
a fluidic channel integrated over the nanostructure.

4. The surface plasmon based sensing device of claim 3, wherein the 3-D composite metallodielectric nanoresonant array is structured to couple propagating surface plasmon polariton (SPP) waves and localized surface plasmon resonant (LSPR) modes.

5. The surface Plasmon based sensing device of claim 4, wherein, in coupling SPP and LSPR,
the 3-D composite metallodielectric nanoresonant array is configured to use an enhanced surface electric field and micro-channel configuration to sense a molecule of interest.

6. The surface Plasmon based sensing device of claim 4, wherein, in coupling SPP and LSPR,
the 3-D composite metallodielectric nanoresonant array is configured to monitor at least one location of the nanoholes to detect molecules near the nanoholes.

7. The surface Plasmon based sensing device of claim 4, wherein, in coupling SPP and LSPR,
the 3-D composite metallodielectric nanoresonant array is configured to be in a through-hole fluidic configuration to detect small molecules.

8. The surface Plasmon based sensing device of claim 4, wherein the 3-D composite metallodielectric nanoresonant array is configured in a pass-through configuration to allow molecules to pass through the nanoholes so as to allow the molecules to sense a maximal local electric field and yield maximal enhancement Raman detection.

9. The surface Plasmon based sensing device of claim 4, wherein the 3-D composite metallodielectric nanoresonant array is configured in a pass-over configuration that includes a microfluidic channel over the 3-D composite metallodielectric nanoresonant array to allow molecules to pass over the nanoholes.

10. The surface Plasmon based sensing device of claim 4, wherein the 3-D composite metallodielectric nanoresonant array is configured to
monitor SPP resonant shift over an area on the 3-D composite metallodielectric nanoresonant array surface to obtain quantity information of molecules on the surface; and
monitor Raman scattering from the nanoholes of the 3D metallodielectric nanoresonant array to identify the molecules.

11. The surface Plasmon based sensing device of claim 4, wherein the 3-D composite metallodielectric nanoresonant array is configured to
monitor LSPR resonant shift over a single or multiple nanoholes to obtain quantity information of molecules near the nanoholes; and
monitor Raman scattering from the nanoholes of the 3D metallodielectric nanoresonant array to fast identify the molecules.

* * * * *